(12) United States Patent
Blair

(10) Patent No.: US 6,575,895 B1
(45) Date of Patent: *Jun. 10, 2003

(54) APPARATUS FOR FACILITATING ANALYSIS OF DREAM ACTIVITY

(76) Inventor: Bruce Blair, 732 W. Bittersweet Pl., Apt. 408, Chicago, IL (US) 60613

( * ) Notice: Subject to any disclaimer, the term of this patent is extended or adjusted under 35 U.S.C. 154(b) by 0 days.

This patent is subject to a terminal disclaimer.

(21) Appl. No.: 09/993,212

(22) Filed: Nov. 16, 2001

Related U.S. Application Data

(63) Continuation-in-part of application No. 09/722,173, filed on Nov. 24, 2000.
(60) Provisional application No. 60/167,564, filed on Nov. 26, 1999.

(51) Int. Cl.[7] .......................... A61M 21/00; A61B 5/04; A61B 19/00
(52) U.S. Cl. .......................... 600/27; 600/26; 600/544; 128/898
(58) Field of Search ..................... 600/27, 544, 26; 128/898

(56) References Cited

U.S. PATENT DOCUMENTS

| | | | | |
|---|---|---|---|---|
| 4,047,377 A | * | 9/1977 | Banks, Jr. .................. | 330/130 |
| 4,228,806 A | * | 10/1980 | Lidow ........................ | 368/12 |
| 4,735,199 A | * | 4/1988 | DiLullo ...................... | 600/28 |
| 4,832,050 A | * | 5/1989 | DiLullo ...................... | 340/573.1 |
| 4,863,259 A | * | 9/1989 | Schneider et al. .......... | 351/209 |
| 5,197,941 A | * | 3/1993 | Whitaker ..................... | 600/27 |
| 5,507,716 A | | 4/1996 | LaBerge et al. | |
| 5,551,879 A | * | 9/1996 | Raynie et al. .............. | 434/236 |
| 6,058,939 A | * | 5/2000 | Goldsmith ................... | 128/898 |
| 6,272,378 B1 | * | 8/2001 | Baumgart-Schmitt ....... | 600/544 |

OTHER PUBLICATIONS

Westclox's "Moonbeam Big Ben" clock, 1940.

* cited by examiner

*Primary Examiner*—William C. Doerrler
(74) *Attorney, Agent, or Firm*—Michael Best & Friedrich LLC

(57) ABSTRACT

A programmable dream analyzer apparatus for assisting the user in recording his or her dreams, comprising a microcontroller for receiving input defining the user's sleep period, and calculating the time and playing an alert for each REM event predicted to occur during the user's sleep period. The strength of each alert may be user adjusted, such that it is sufficient to wake the user during a REM event, but not during non-REM sleep. The dream analyzer further incorporates a voice activated recording device to allow the user to record a description of his or her dream upon awaking from a REM event without moving.

40 Claims, 10 Drawing Sheets

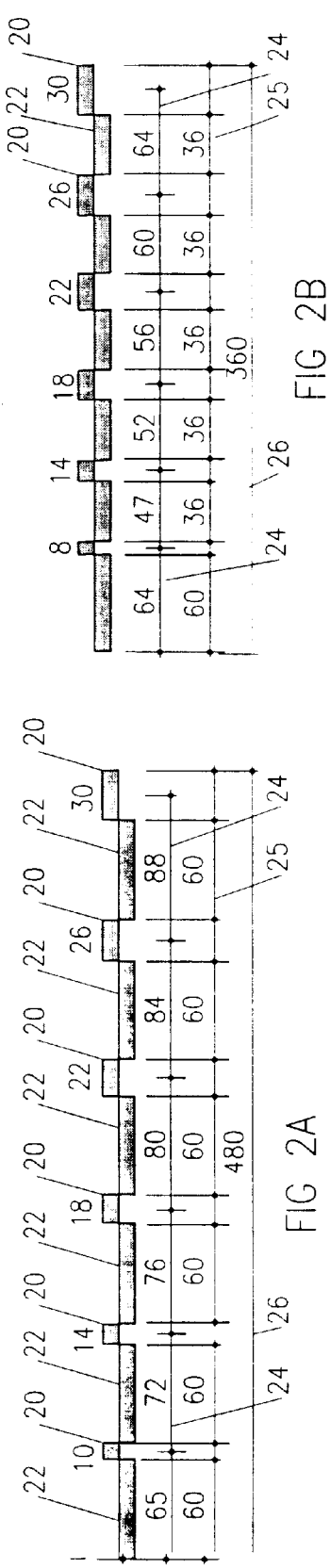
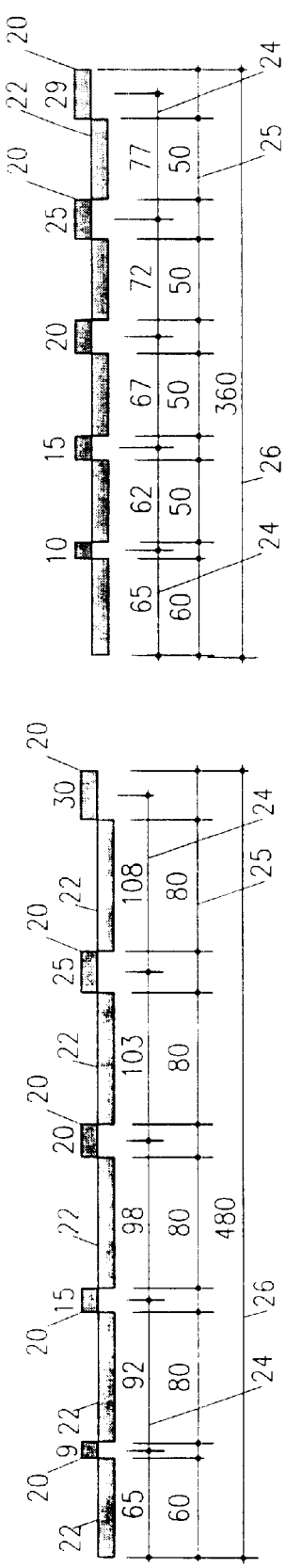
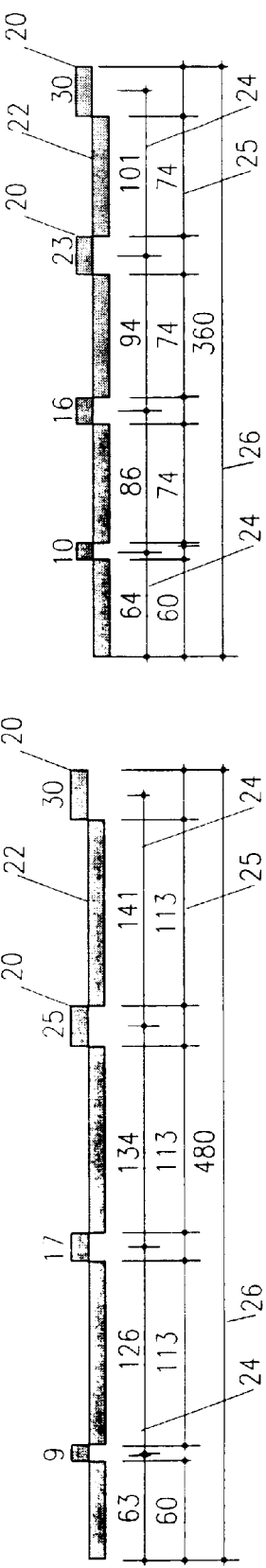

APPARATUS FOR FACILITATING ANALYSIS OF DREAM ACTIVITY

RELATED APPLICATIONS

This application claims priority as a continuation-in-part of application Ser. No. 09/722,173 filed on Nov. 24, 2000, which claims priority of provisional Application Ser. No. 60/167,564 filed on Nov. 26, 1999.

FIELD OF THE INVENTION

The present invention provides a method and apparatus enabling a user to investigate his or her nightly dream activity with little or no loss in the restorative process of a good night's sleep.

BACKGROUND OF THE INVENTION

The use of dreams as an anecdotal source of inspiration and prophecy is so common as to be recognizable across cultures, both current and through the ages. Mythological references to dreams and their effects abound. More recently, dreams have been made the basis of mental health inquiries through psychoanalysis. Individuals discussing their dreams with family and friends is an experience shared by all. Many inventors, scientists and artists have reported dream activity as the basis of many of their creative accomplishments.

A few devices have been developed over the years to analyze dreams and enhance the dreamer's memory of his or her dreams. However, the prior art has mainly focused on one notable aspect of dream activity: the so-called "Lucid Dream". The lucid dream is a dream in which the dreamer is aware of dreaming while remaining in the dream state. This arcane condition is often the focus of sleep labs and research institutes. Such facilities have developed devices to sense a sleeper's dreaming or non-dreaming state.

In general, these devices are worn by the test subject in order to sense the dream state. When a dream state is detected some form of feedback is provided to alert the patient that a dream is occurring. If all works out well, a lucid dream will ensue. The prior art all require some form of device that is physically attached to the sleeper. Wearing such an attachment is not a normal part of the sleeper's habits and can interfere with the test subject's usual night's sleeping process and may itself become the focus of the subject's dream activity.

For example, LaBerge et al. U.S. Pat. No. 5,507,716 discloses a mask, similar to sunglasses or goggles, which is additionally wired for sound. Such devices may be suitable for investigating sleep patterns in a lab context, but are not likely to find widespread nightly usage among the general populous. Additionally, the devices described by Laberge et al. are expensive, further limiting their appeal to individuals who may desire to investigate their dreams on their own.

Many experiments have been performed to awaken test subjects during the so-called REM (Rapid Eye Movement) periods of sleep. It has been determined that these periods usually correspond with dream activity. When a test subject is awakened during a REM event, the subject is usually able to remember the dream which was occurring at the time he or she was awakened. If the test subject is not awakened, the dream is more likely to be forgotten during the intervening periods of deeper, dreamless sleep. Thus, for those individuals who are interested in investigating the subjects of their dreams it is desirable that they occasionally be woken up either during or shortly after a REM event. With most subjects, the first REM event usually occurs about sixty minutes after the subject falls asleep. Thereafter, periods of deep sleep with little dream activity are punctuated by periods of heightened dream activity during REM events which occur approximately every 90 minutes.

Most persons experience a cycle of 4, 5 or 6 REM events per night.. These cycles are usually consistent for a given individual but vary from one person to another. In a substantial percentage of the population the rhythms are so strong and consistent that many people have no need for an alarm clock. Their own "internal clocks" are so accurate that they wake up at the same time each morning on their own. This indicates that for many individuals it is not necessary to provide sensors and or physical hookups to the individual to determine when REM events are taking place since the REM events will take place at substantially the same time each night.

For those persons having a sufficiently regular sleeping rhythm, a remote device could be programmed to awaken the individual at the appropriate time at the end of or just after the conclusion of a REM event. Such a device could be configured to wake the dreaming individual by issuing an "alert" in the form of flashing lights, playing sounds at certain frequencies, playing music, and so forth. As REM sleep is much closer to the waking state than non-REM sleep, the strength of the alert would be set at a level which would only awaken the user during a REM event. Such a device would ideally allow for variable time settings in order to individually synchronize the occurrence of dream alerts with an individual's nightly rhythms. Dream alerts could be set to occur, for example, at the end of the individual's REM events or shortly thereafter.

Such synchronization could be effected through repeated use and fine tuning of the dream alert settings. Reliable timing will proceed from the daily stored and updated values of the alert variables. By fine tuning the synchronization between the dream alerts and the occurrence of REM events, the dream alerts may be provided by a remote device with no physical connections to the user. The user would then experience a more natural sleep environment while still benefiting from being awakened during and usually near the end of REM events so that dreams are more fully remembered. An additional desirable feature of such a device would be to include a dictation system so that the user could record the subject matter of his or her dreams before returning to sleep. Further, the user's normal sleep patterns such as the time the individual normally goes to bed and gets up should be storable so that the user need not go through a tedious set up procedure each night before retiring. The nature of the dream alerts should also be selectable to allow for a wide range of wake up options. For example, device settings should allow for minimal intrusion during the REM cycle. This will help to prevent waking the user during non-REM periods, as well allowing the user to complete dreams before the user awakens in response to the alert event.

SUMMARY OF THE INVENTION

These needs and other needs are satisfied by the present invention comprising a programmable dream analyzer apparatus containing a programmable microcontroller, at least one input device operatively connected to the microcontroller, and an alert device or alert enunciator connected to the microprocessor. The microcontroller is adapted to receive user input consisting of a start time corresponding to a time when the user goes to sleep, and an end time corresponding to a time when the user expects to wake up. Alternatively, the user may input his or her total sleep time instead of the wake up time.

The microcontroller then calculates and programs the times for an alert that are associated with the occurrence of a REM event that the user is expected to experience in the time period between the start time and end time. The microcontroller then activates an alert device or alert enunciator at the programmed alert times, such as flashing LEDs or playing a melody or tone through a speaker.

BRIEF DESCRIPTION OF THE DRAWINGS

FIGS. 2A and 2B illustrate a timeline showing the periodicity of dream intervals with six REM events within an eight hour and six hour period, respectively.

FIGS. 3A and 3B illustrate a timeline showing the periodicity of dream intervals with five REM events within an eight hour and six hour period, respectively.

FIGS. 4A and 4B illustrate a timeline showing the periodicity of dream intervals with four REM events within an eight hour and six hour period, respectively.

DETAILED DESCRIPTION OF INVENTION

In accordance with the present invention, a dream analyzer apparatus is described, which operates to wake a sleeping individual at predetermined times corresponding to the individual's pattern of nightly REM event cycles. In general, dreams that occur during REM events are usually forgotten during the next non-REM interval. Thus, an individual is more likely to remember the details of a dream or dreams that occurred during the REM event if he or she awakes at or near the end of an REM event, than if the individual remained sleeping.

The inventive dream analyzer includes a voice activated recording system whereby, upon waking up during or shortly after a dream, an individual may dictate a description of the dream to the apparatus. The dream analyzer records the individual's spoken message for later playback when the individual is awake. In this way, an individual may preserve many vivid details of the dreams that are normally forgotten when the individual returns from REM to non-REM sleep.

Figure 1:
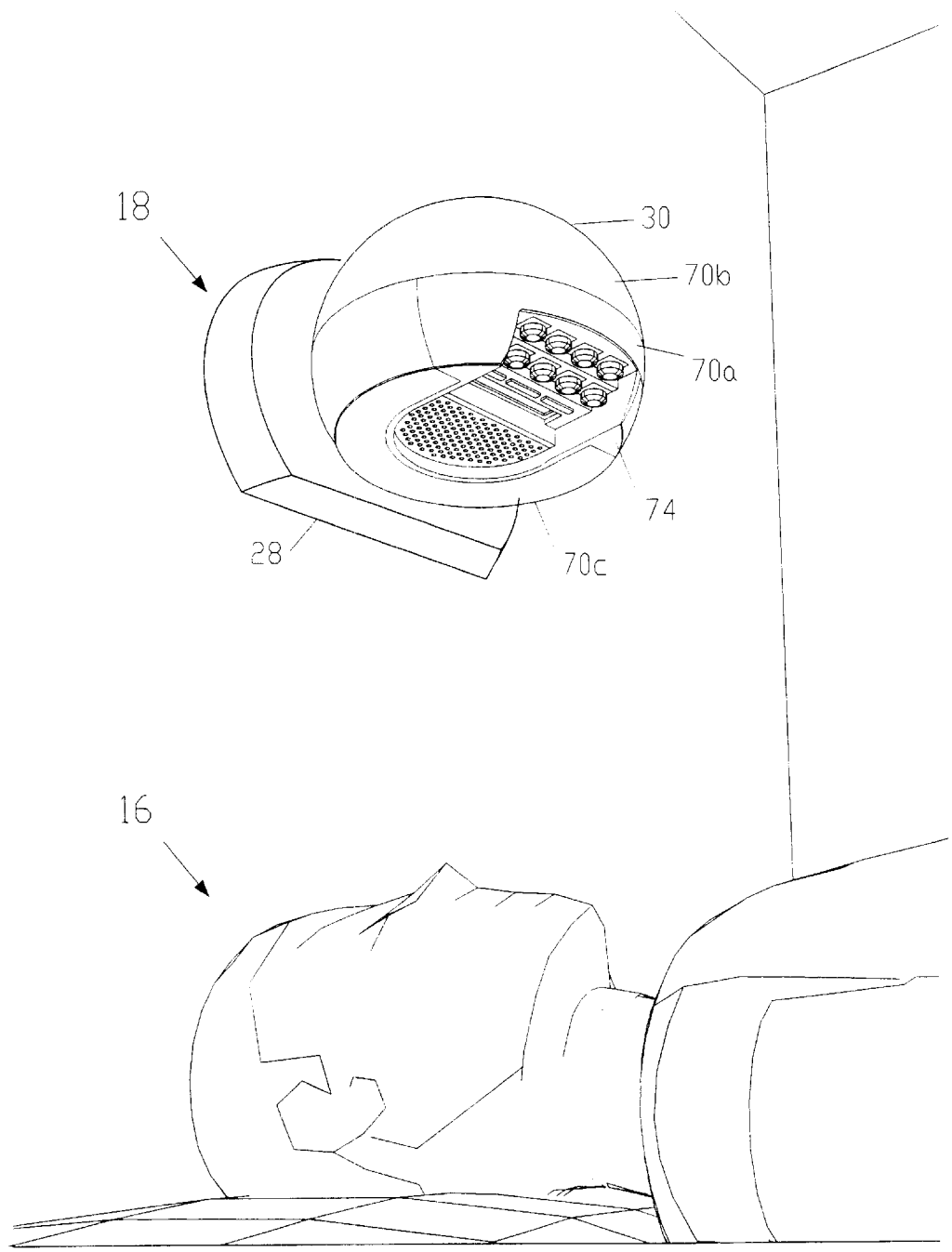
FIG. 1 is a perspective view of the inventive dream analyzer apparatus shown in relation to the user.
Figure 5:
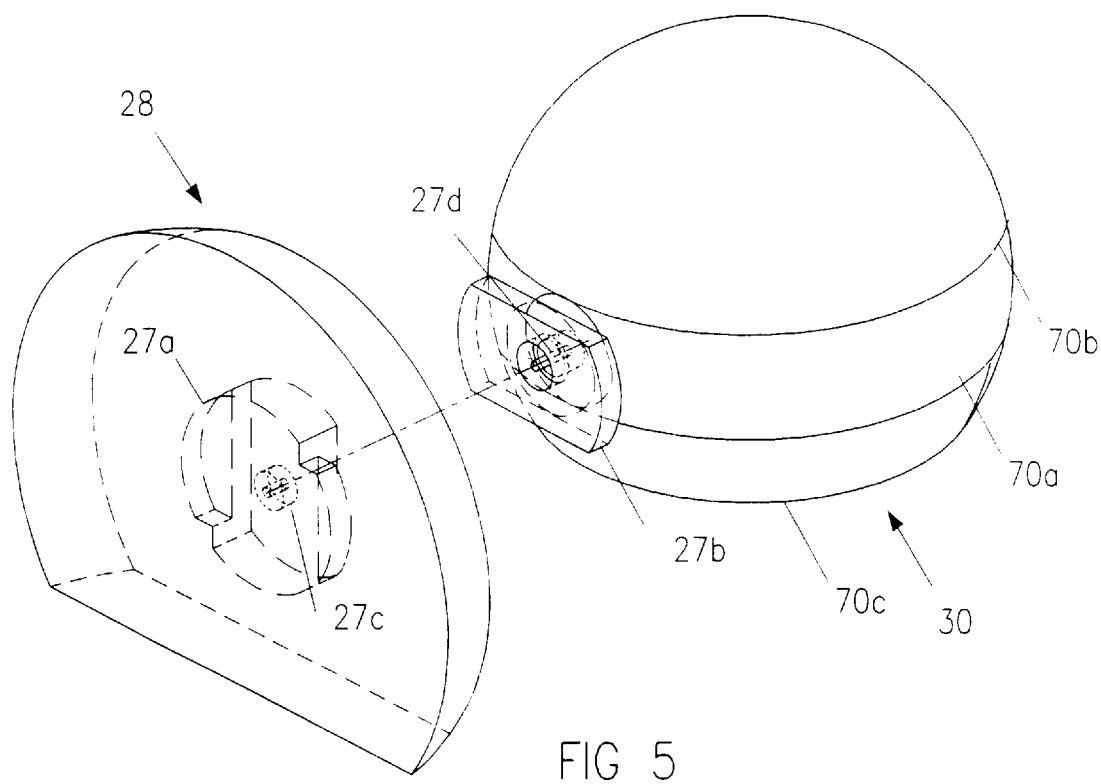
FIG. 5 is a top perspective view of the dream analyzer apparatus of FIG. 1 seen from behind, showing the assembly of the electronic unit on the wall mounting plate.
Figure 6:
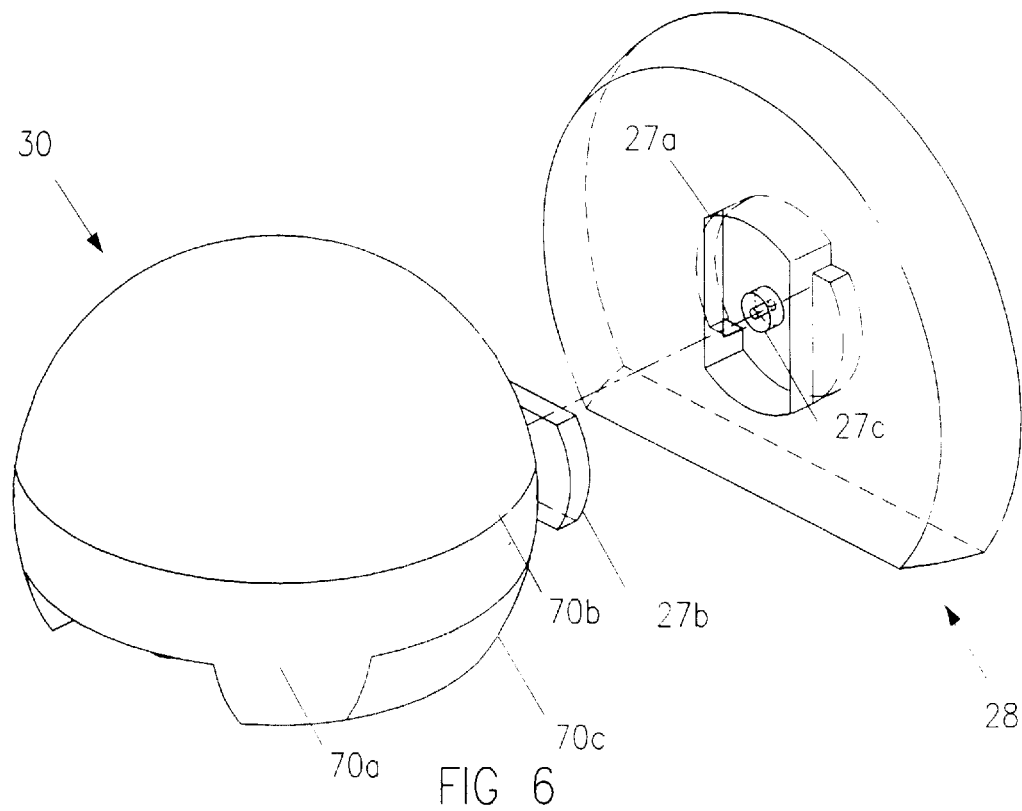
FIG. 6 is a top perspective view of the dream analyzer apparatus of FIG. 5 seen from the front.

FIG. 1 shows the inventive dream analyzer apparatus 18 mounted to a wall or the head board of a bed above a sleeping individual 16. Dream analyzer 18 operates by playing a series of alert event devices to wake individual 16 at predetermined times corresponding to the individual's nightly pattern of REM event cycles. The time and nature of each alert is fully programmable, so that individual 16 can customize dream analyzer 18 to his or her individualized sleeping patterns and habits. Optimal results are achieved when the individual using dream analyzer 18 has regular sleep habits, such as going to bed at or near the same time each evening and rising at substantially the same time each morning. Under these conditions, REM events are most likely to occur at or near predictable times each night.

In order to fully appreciate the operation of the inventive dream analyzer apparatus, it is first necessary to review the sleeping patterns common to most people. The sleep period for most individuals ranges from 6 to 10 hours, and usually varies with the age of the user. Older children and younger adults may require up to 10 hours of sleep, while the elderly require, on average, 6 or even fewer hours of sleep a night. Thus, dream analyzer 18 provides for up to a 12-hour sleep period, with the actual time settings typically determined by the age of the user.

Most individuals experience 4, 5 or 6 REM event cycles during each sleep period. The first and last REM events typically occur at the same relative time, regardless of the length of the sleep period or the number of REM events. The first REM event occurs approximately 60 minutes after the individual falls asleep and usually lasts about 10 minutes. The last REM event of the night occurs approximately 30 minutes before the end of the sleep period and typically ends when the individual wakes up. In general, the remaining REM events are evenly spaced between first and last REM events, and increase in length as the sleep period progresses.

For example, FIGS. 2A and 2B, 3A and 3B, and 4A and 4B respectively depict the REM event cycles of individuals having 4, 5 or 6 REM events per night. FIGS. 2A, 3A and 4A depict the REM event cycles of individuals over an 8-hour sleep period, while FIGS. 2B, 3B, and 4B depict the REM event cycles over a 6-hour sleep period. In general, individuals who have a sleep period in the 6-hour range will experience 4 REM event cycles per night (FIG. 4B), while those in the 8-hour range will experience 5 or 6 REM event cycles per night (FIGS. 2A, 3A). A 10-hour sleep period is not shown but would be proportional to the sleep periods shown FIGS. 2A and 2B, 3A and 3B, and 4A and 4B.

Each such figure depicts a graph of an individual's sleep period, with time extending along the horizontal axis. The longer, lower shaded portions represent intervals of deep sleep 22, while the upper shaded portions represent REM events 20. The series of numbers above REM events 20 represent the duration of each REM event in minutes. Line 24 shows the REM event cycles, with the series of numbers above line 24 indicating the amount of time for each cycle, as measured between the midpoints of adjacent REM events 20. Similarly, line 25 shows the amount of time for each interval of deep sleep 22 between REM events 20. Finally, line 26 shows the total amount of time for the sleep period.

As can be seen in FIGS. 2A and 2B, 3A and 3B, and 4A and 4B, the duration of the REM events 20 increases as the night wears on, while the duration of the intervals of deep sleep 22 remains substantially constant. For example, FIG. 4B shows an individual who experiences 4 REM event cycles in a 6-hour (360 minute) sleep period. The duration of the REM events 20 increases in time from 10 minutes for the initial REM event to 16, 23 and 30 minutes for subsequent REM events. The REM events are evenly spaced between 74 minute intervals of deep sleep 22. Thus, if that individual desired to be awakened for each REM event, dream analyzer 18 would be programmed to play a series of alerts at the midpoint of each REM event 20, approximately 64, 150, 244 and 345 minutes after first falling asleep.

Dream analyzer 18 may be programmed to wake the user at appropriate times by simply inputting the time for going to bed at night and getting up in the morning, to define the total amount of time for the sleep period. Dream analyzer 18 will then calculate and set the time for a series of alerts based on the 4, 5 and 6 REM event cycles. The user may further program dream analyzer 18 by individually rescheduling each alert.

Figure 9:
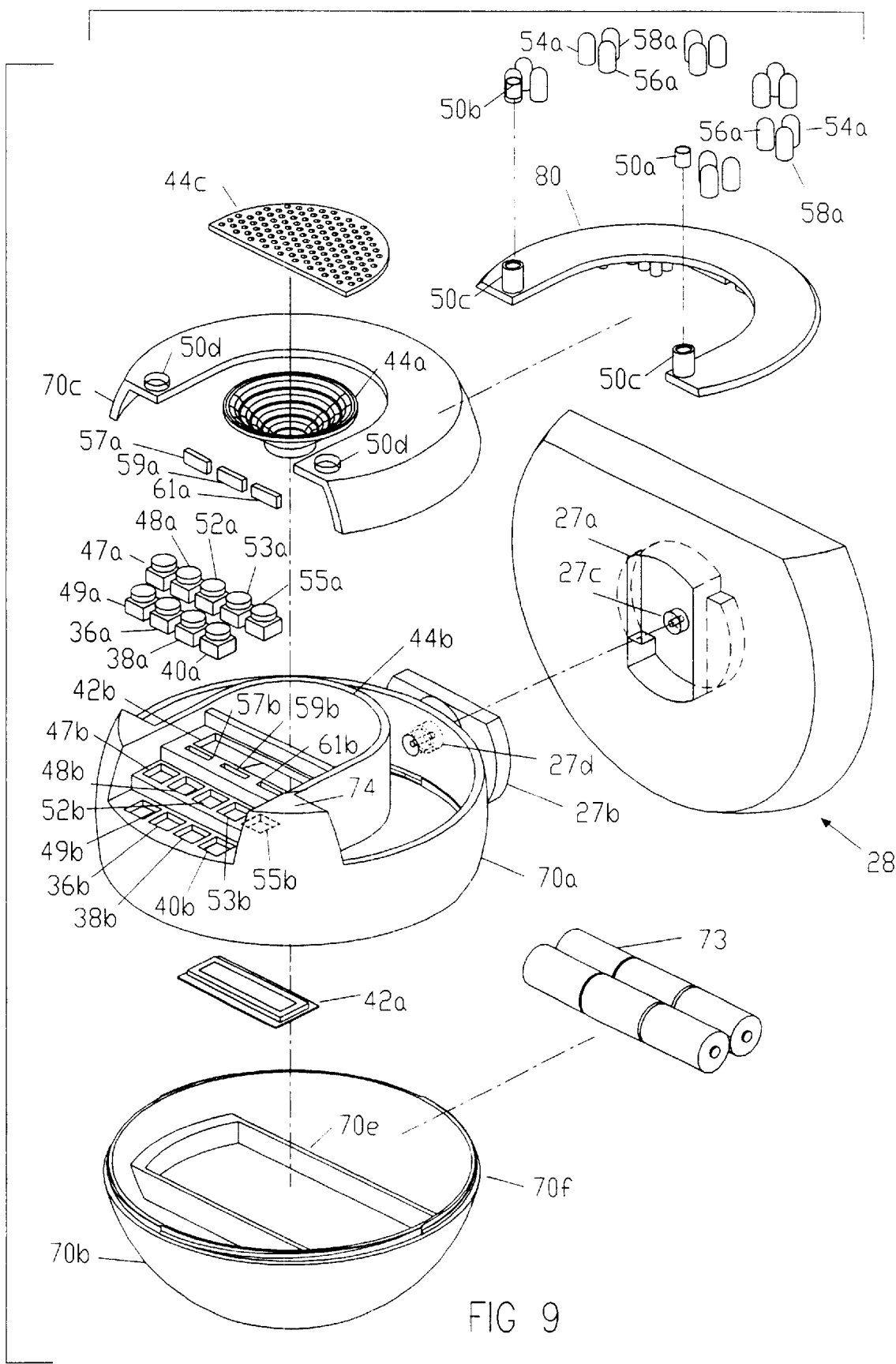
FIG. 9 is an inverted, exploded bottom perspective view of the dream analyzer apparatus of FIG. 1 seen from the front.
Figure 10:
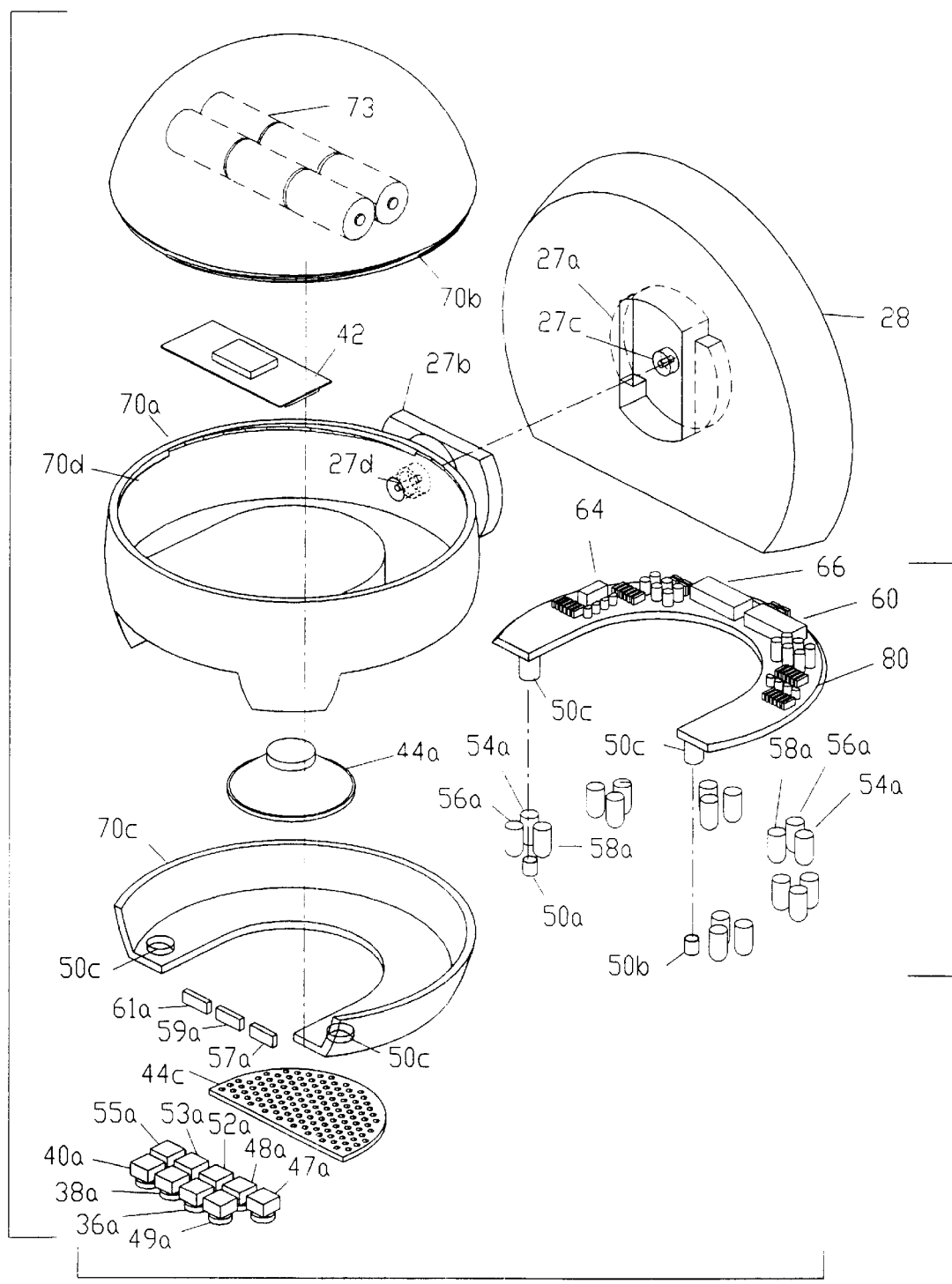
FIG. 10 is an exploded top perspective view of the dream analyzer apparatus of FIG. 9 seen from the front.

Dream analyzer 18 is also programmable in the sense that the user may adjust the strength of each alert with respect to several variables to fit his or her own preferences. In particular, the strength of the alert may be adjusted so that it is sufficient to wake the user during a REM event when the user is closest to the waking state, but not during non-REM, deep sleep. In one embodiment of the invention, the dream analyzer 18 is provided with an alert device or alert enunciator, such as flashing Light Emitting Diodes (LEDs) 54a, 56a and 58a directed toward the sleeping user, as best shown in FIGS. 9 and 10. Alert LEDs 54a, 56a and 58a are arranged in a plurality of triads of red 54a, green 56a and blue 58a diodes. The user may adjust the color emitted by alert LEDs 54a, 56a and 58a by programming dream analyzer 18 to flash either one or a combination of red, green and blue diodes in each triad. The user may also adjust the overall intensity of alert LEDs 54a, 56a and 58a, as well as the number, duration and length of time between flashes.

The required alert strength varies not only between individuals, but also at different times of the night for the same individual. Thus, if a user is particularly interested in dreams that occur in early REM events, he or she may program dream analyzer 18 to increase the strength for alerts that occur early in the night, and reduce the strength for later alerts. The user may further program a ramp function wherein the intensity of flashing alert LEDs 54a, 56a and 58a gradually decreases and increases over the course of an alert. The least intensity that will awaken the user will also usually awaken the user latest in the REM event and, thus, offer most of the dreaming sequence for vocal notation.

The alert device may also play an accompanying sound which is selectable by the user, such as a melody, tone, or other alert sounds that are well known in the art. Dream analyzer 18 may be programmed such that the early, middle and late alerts may each have their own alert sound. Silence also may be selected and the alert sound volume is adjustable. As the entire program fills approximately only 60% of the memory capacity of a microcontroller, such as the PIC16F876 chip (Microchip Technology Inc.—Itasca, Ill.), space for two dozen songs is available.

Dream analyzer 18 will now be described with regard to FIGS. 1, and 5–10. FIG. 1 shows dream analyzer 18 properly positioned for use by a sleeping individual 16. Dream analyzer 18 comprises an electronic unit 30 rotatably mounted on a mounting plate 28, that is attached to a vertical support above the head of a sleeping individual 16, such as a wall or headboard of a bed, by screws, adhesive or other means well known in the art (not shown).

Electronic unit 30 comprises a bottom casing 70a, an upper casing 70b, and a transparent lens 70c. As best seen in FIGS. 5–10, electronic unit 30 is assembled on mounting plate 28 by means of a tab 27b, which projects from the rear of bottom casing 70a. A slotted opening 27a is formed in the center of the mounting plate 28, and is configured to rotatably receive tab 27b. Electronic unit 30 is assembled on mounting plate 28 by inserting tab 27b into slotted opening 27a and rotating 90 degrees to lock tab 27b in place within slot 27a and fix electronic unit 30 in its proper position on mounting plate 28.

The power for the unit electronic 30 is primarily provided by a 600 mA/6 V wall outlet transformer with appropriate cord and plug (not shown), as is well known in the art. To accommodate the transformer plug, a recessed power jack 27d is formed in tab 27b, which accepts a complementary projection plug 27c cast within the slot 27a of mounting plate 28.

Upper casing 70b is removably attached to lower casing 70a by means of complementary threads 70d, 70f, respectively formed in lower casing 70a and upper casing 70b. As shown in FIGS. 9 and 10, threads 70d and 70f accommodate a 90 degree rotation. The removable upper casing 70b provides convenient access to the battery carriage 70e, which is integrally formed within upper casing 70b. Battery carriage 70e is configured to hold 6 AA-type batteries 73, which provide backup power when the electronic unit 30 is removed from mounting plate 28 and is disconnected from the wall outlet transformer.

Lens 70c is permanently attached to lower casing 70a by welding, gluing or other means well known in the art.

The instrumentation and display for operating dream analyzer 18 is mounted on underside 74 of electronic unit 30, so as to face the user sleeping below. A single row, 16-character Liquid Crystal Display (LCD) screen 42a with an integral backlight 43 (shown in FIG. 12), such as an Optrex DMC 16105NY-LY produced by Optrex America, Inc. (Plymouth, Mich.), is mounted in an opening 42b in bottom casing 70a. A speaker 44a, such as a LabTech SS-11 (Andover, Mass.) is mounted within a housing 42b formed in bottom casing 70a, and concealed behind a screen 44c. A series of indicator LEDs 57a, 59a and 61a are mounted within complementary slots 57b, 59b and 61b in bottom casing 70a, and provide visual confirmation of the status of the recording system as described below.

Figure 8:
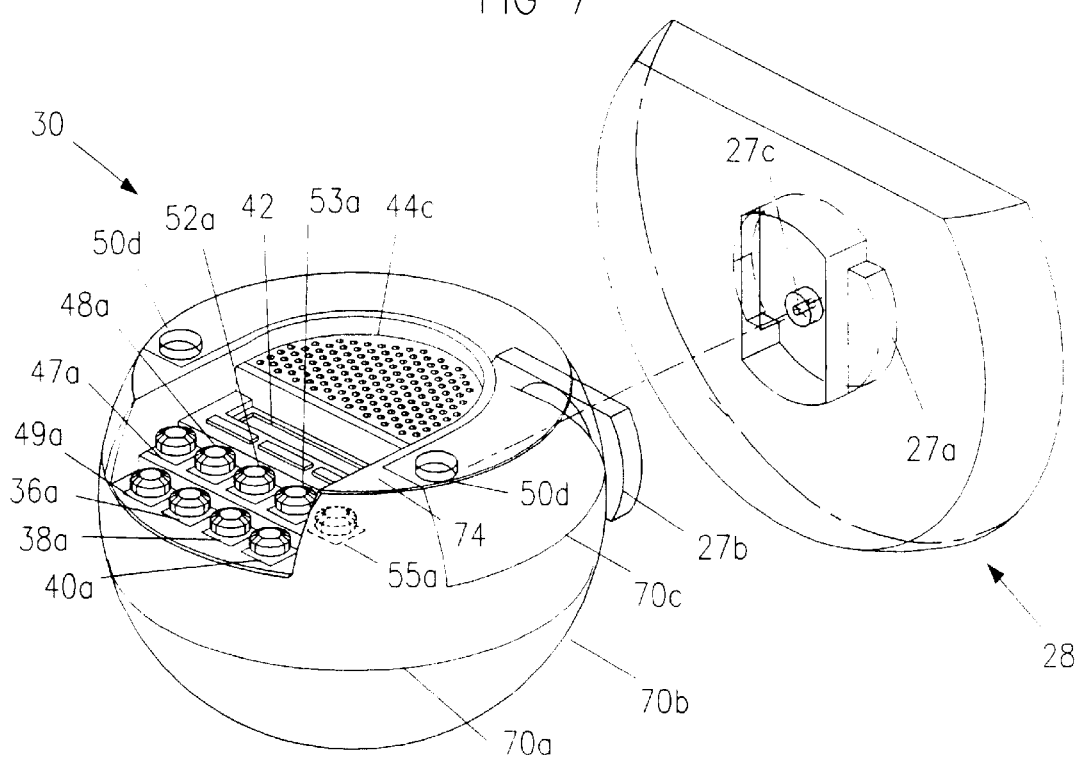
FIG. 8 is an inverted, bottom perspective view of the dream analyzer apparatus of FIG. 7 seen from the front.

As best shown in FIGS. 8 and 9, a plurality of momentary pushbutton operators 36a, 38a, 40a, 47a, 53a and 55a, such as Mountain Switch momentary, 107 DS-622, and latching operators 48a and 52a, such as Mountain Switch on-off switch, also 107 DS 622, (Mouser, Mansfield, Tex.) and a one megaohm potentiometer 49a, such as Digi-Key CT2271-ND (Thief River Falls, Minn.) are positioned on the underside 74 of the electronic unit 30, mounted within complementary slots 36b, 38b, 40b, 47b, 48b, 49b, 52b, 53b and 55b in bottom casing 70a. The pushbuttons include a device on/off button 48a, a playback/record button 52a, a voice chip reset button 53a, a voice chip start/pause button 55a and a device reset button 47a. In addition, electronic unit 30 is provided with a quartet of device programming pushbuttons comprising left, middle and right pushbuttons 36a, 38a, and 40a, and a rotatable alert sound volume button 49a. Buttons 36a, 38a and 40a have varying functionality in the input of user information and programming of dream analyzer 18, as described below.

In alternative embodiments, other input devices may be utilized as well as the pushbutton operators 36a, 38a, 40a, 47a, 48a, 49a, 52a, 53a and 55a, such as an infrared remote control device, as is well known in the art. In yet another embodiment, dream analyzer 18 is provided with an input/output jack and direct reprogramming of microcontroller 60 is enabled, as is well known in the art, to permit downloading of alert presets, songs, tones or other information stored in a computer or similar device, or from an Internet web site.

A pair of electret microphones 50a, 50b and a series of alert LEDs 54a, 56a and 58a are concealed behind lens 70c. As shown in FIGS. 9 and 10, a printed circuit board 80 is mounted within bottom casing 70a, behind lens 70c. LEDs Microphones 50a, 50b are installed in sound mounts 50c attached to circuit board 80 and positioned above openings 50d in lens 70c. A plurality of alert LEDs 54a, 56a and 58a are also connected to circuit board 80 behind lens 70c, arranged in a series of triads encircling LCD 42a, each triad comprising a red 54a, green 56a and blue 58a alert LED. Alert LEDs 54a, 56a, and 58a, are preferably 10 mm narrow view diodes having at least 8000 mll luminosity, such as those provided by Marktech Optoelectronics (Menands, N.Y.), but other comparable LEDs or lamps may be used. As alert LEDs 54a, 56a and 58a have a 10 year life expectancy, the lens 70c is permanently mounted to lower casing 70a.

Figure 12:
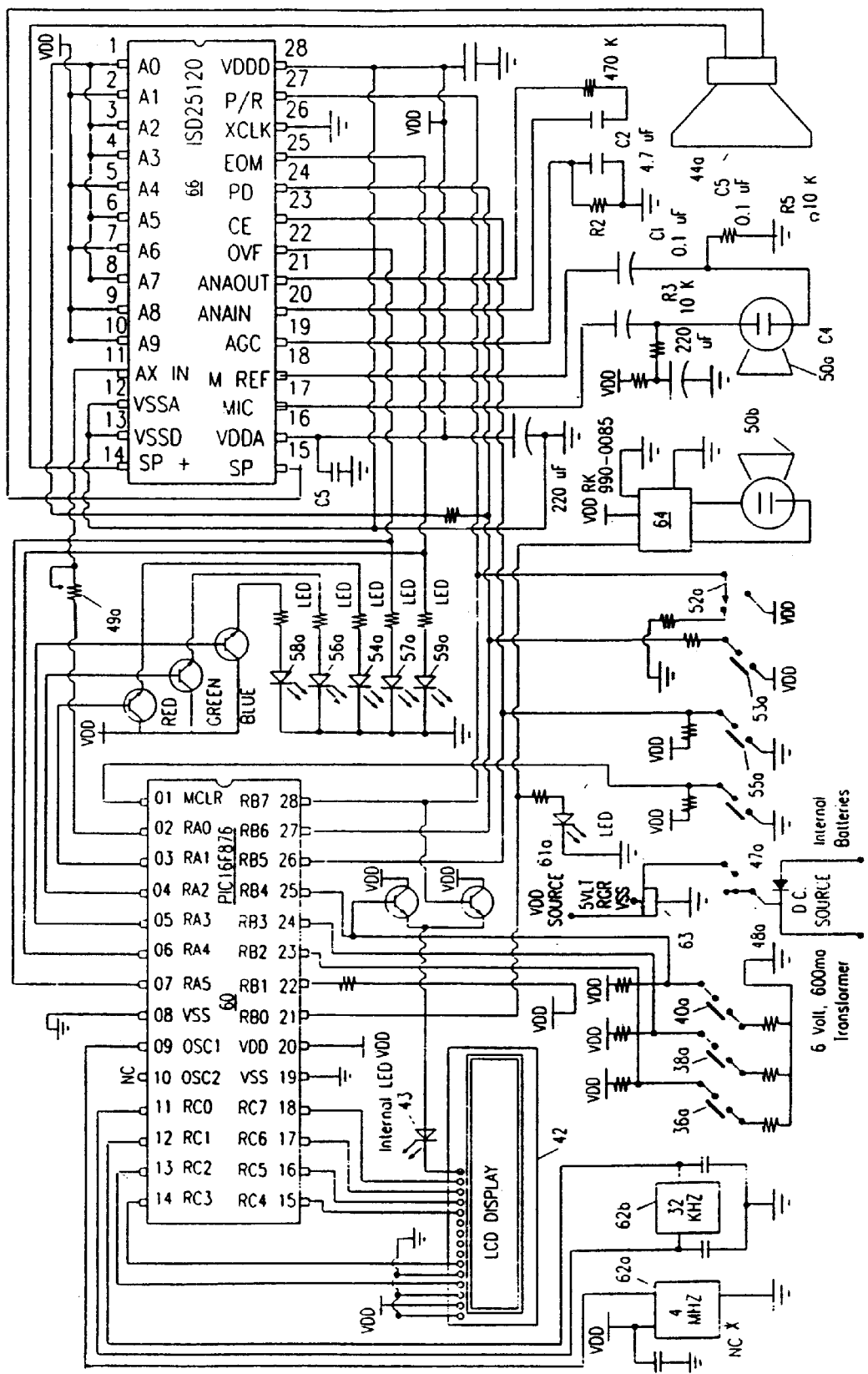
FIG. 12 is a schematic electrical circuit diagram of the inventive dream analyzer apparatus.

As shown in the diagram of FIG. 12, printed circuit board 80 includes a microcontroller 60, a voice recording/playback chip 66 and a voice activated switch 64. In a preferred embodiment, microcontroller 60 is a PIC16F876 chip, voice recording/playback chip 66 is an ISD25120 chip (WINBOND/ISD, Inc.—San Jose, Calif.), although those skilled in the art will appreciated that other chips with similar functions may be used. If a PIC16F876 chip is used, the following chip fuses should be programmed along with the hex code supplied.

| Oscillator: | XT |
|---|---|
| Watchdog Timer | Off |
| Power Up Timer | On |
| Code Protect | Off |
| Brown Out Detect | Off |
| Low Voltage Program | Off |
| Flash Program Write | Off |
| Background Debug | Disabled |

Voice activated switch 64 is an Rk 990-0085 switch (Electronic Rainbow Inc. —Indianapolis, Ind.). The circuit diagram for voice switch 64 indicates a one megaohm pot may be used as an alternate for a supplied resistor to tune the sensitivity of the switch, as is well known in the art. Operating power for the components mounted on circuit board 80 is provided by wall outlet transformer or by batteries 73 through a +5 volt voltage regulator with suitably sized and mounted heat sink 63, as shown in FIG. 12.

FIG. 12 shows the connections between voice recording/playback chip 66, speaker 44a, and one of the microphones 50a. The second microphone 50b is connected to voice activated switch 64, which, in turn, is input to the RB0 interrupt line of microcontroller 60. The output from voice activated switch 64 controls the record function of voice recording/playback chip 66, as modified by the programming output of microcontroller 60.

During a programmed alert, dream analyzer 18 enables voice activated switch 64 and turns on LCD screen backlight 43 in preparation for receiving the dictated description of the user's dream. The sound of the user's voice activates switch 64, which, in turn, signals microcontroller 60 to activate voice recording/playback chip 66 and record the user's dictation. Voice recording/playback chip 66 further activates indicator LED 61a to provide visual confirmation that the recording system is activated. As the recording device is a solid state voice recording/playback chip 66 rather than tape, a syllable may be slightly clipped, but beginning words are usually not completely lost or unintelligible.

Because the brain represses physical movements during dreaming, a dream will usually be forgotten if a dreamer initially moves after waking without first mentally reviewing the dream. For this reason, the combination of voice-activated switch 64 and voice recording/playback chip 66 allows the user to record a description of his or her dream without requiring the user to move. In addition, not moving permits the user to quickly fall back into non-REM slumber after the record of the dream is made. On arising the following morning, the user may playback the dream recorded during the night by pressing playback/record button 52a in conjunction with voice chip start/pause button 55a, as indicated by step 200, allowing the user to remember the dream that would otherwise probably have been forgotten.

Voice recording/playback chip 66 has a two minute record time, which may be extended by cascading additional chips 66, as is well known in the art. To conserve recording capacity, pauses in dictation or short silences of approximately two seconds will temporarily turn off voice recording/playback chip 66 and indicator LED 61a, until the sound of the user's voice once again activates switch 64.

For each programmed alert, microcontroller 60 resets an internal pointer to the beginning of voice recording/playback chip 66's message storage. Thus, if voice activated switch 64 is activated during more than one alert, the recording made during the last alert will partly or wholly overwrite the earlier recordings. In addition, the user may manually reset voice recording/playback chip 66's internal message pointer to the beginning by pressing reset button 53a or by pressing playback/record button 52a. In an alternative embodiment, dream analyzer 18 is able to save multiple recordings made during different alerts. Increased storage for multiple messages may be obtained by cascading additional recording/playback chips 66 and providing the appropriate code for microcontroller 60, as is well known in the art.

To provide visual confirmation and ensure that dream analyzer 18 is not inadvertently left in manual playback mode, which would prevent voice activated recording during alerts, LCD screen backlight 43 is on during the play mode for voice recording/playback chip 66, but is other wise off except for programming and alert event times.

The playback function is controlled by the play/record pushbutton 52a, the voice chip reset by button 53a and the start/pause function by button 55a, all of which are connected as shown in FIG. 12. Various biasing, filtering and voltage regulating components are also connected as shown in FIG. 12.

Microcontroller 60 is further connected to a 4 MHz oscillator 62a through OSC1 input at pin 9, to provide the clock input for operation of microcontroller 60. A 32 kHz oscillator 62b, commonly known as a watch crystal, is connected to microcontroller 60 at pins RC1 and RC2, to provide a very accurate clock time for user inspection at any time during nominal operation of dream analyzer 18. Device programming pushbuttons 36a, 38a, and 40a are connected to microcontroller 60 through inputs RB2, 3, and 4 at pins 23, 24, and 25, respectively. Microcontroller 60 drives alert LEDs 54a, 56a and 58a through outputs RA1, RA2 and RA3, pins 3, 4, and 5. Microcontroller 60 in combination with voice recording/playback chip 66 also drives backlight 43 for LCD screen 42a through output RB7, pin 28; RB5, pin 26 or playback/record button 52a. Microcontroller 60 also plays the programmed melody or other alert sound at the beginning of an alert through the RA0 pin, which is connected to the auxiliary pin 12 in voice recording/playback chip 66. Various biasing resistors and operating voltages are connected to the microcontroller 60, voice recording/playback chip 66 and voice activated switch 64, as shown.

Microcontroller 60 automatically turns on backlight 43 for LCD screen 42 during an alert, the programming of electronic unit 30 or during a test of the programmed alerts. Backlight 43 turns off to conserve power after the alert, programming or test is complete. However, except during an alert or device programming, the user may manually activate voice recording/playback chip 66 and backlight 43 at any time by pressing latching playback/record button 52a to initiate Playback or Record mode and then pressing momentary reset button 53a and then the momentary chip enable button 54a.

Dream Analyzer 18 operates by playing an alert, such as flashing alert LEDs 54a, 56a and 58a, for each REM event during the user's sleep period. In a preferred embodiment, dream analyzer 18 does not require the user to determine in advance the number of REM events cycles he or she will experience, but calculates an alert for every REM event predicted to occur during a 4, 5 and 6 REM event cycle. Although the 4, 5 and 6 REM event cycles total 15 REM events (4 +5 +6), the first and last REM events in each cycle take place at the same time. Thus, dream analyzer 18 calculates and programs a total 11 separate alerts, any or all of which may be enabled or reset by the user.

The user inputs the start time and end time of his or her sleep period using device programming buttons 36a, 38a and 40a. Dream analyzer 18 automatically calculates the time and programs an alert for each REM event predicted to occur during the user's input sleep period, according to the proportionate ratios shown in FIGS. 2A, 2B, 3A, 3B, 4A and 4B. The user may then reprogram dream analyzer 18 to reschedule, set or clear any of the 11 automatically calculated alerts, as illustrated by the flowchart of the steps of programming and operation of dream analyzer 18 shown in FIGS. 11a, 11b and Appendix A. The flowchart is generally divided into three levels of programming steps 82a, 82b and 82c, each successive level providing more detailed control of the functions of dream analyzer 18. Appendix A shows the software program for a PIC16F876 microcontroller chip in hexadecimal code, enabling the operation of dream analyzer 18 as described by the flowchart of FIGS. 11a and 11b.

Figure 7:
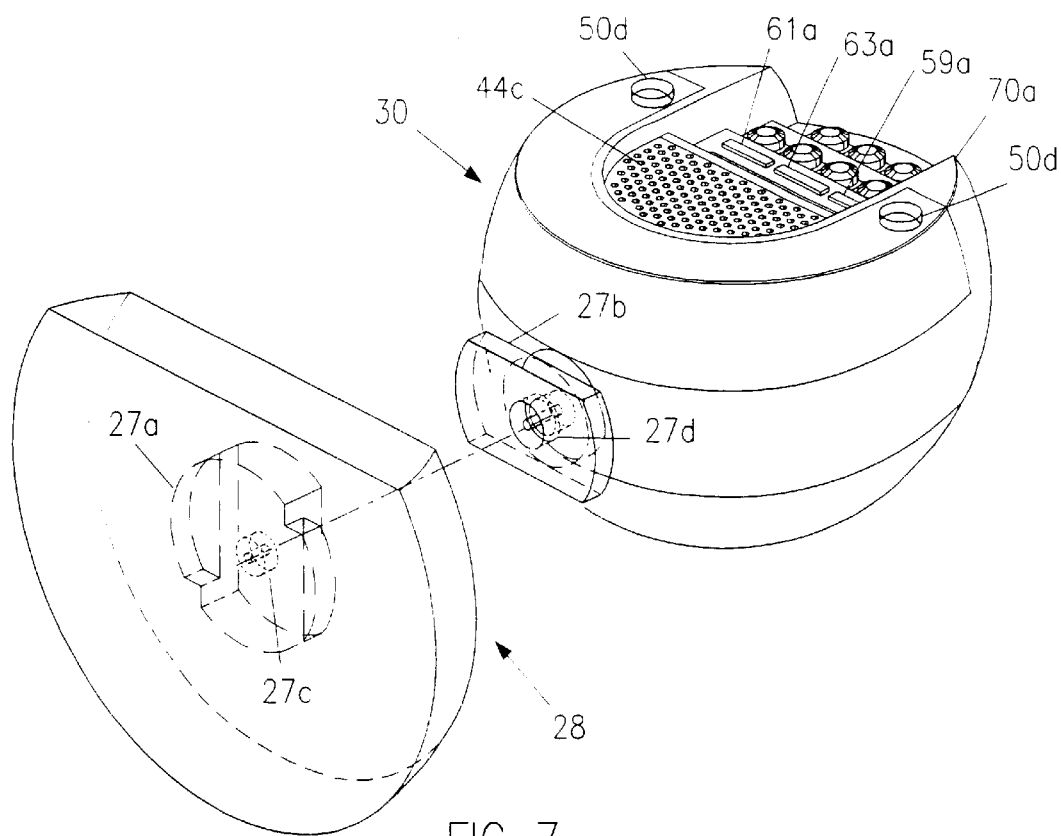
FIG. 7 is an inverted bottom perspective view of the dream analyzer apparatus of FIG. 1 seen from behind, showing the assembly of the electronic unit on the wall mounting plate.
Figure 11A:
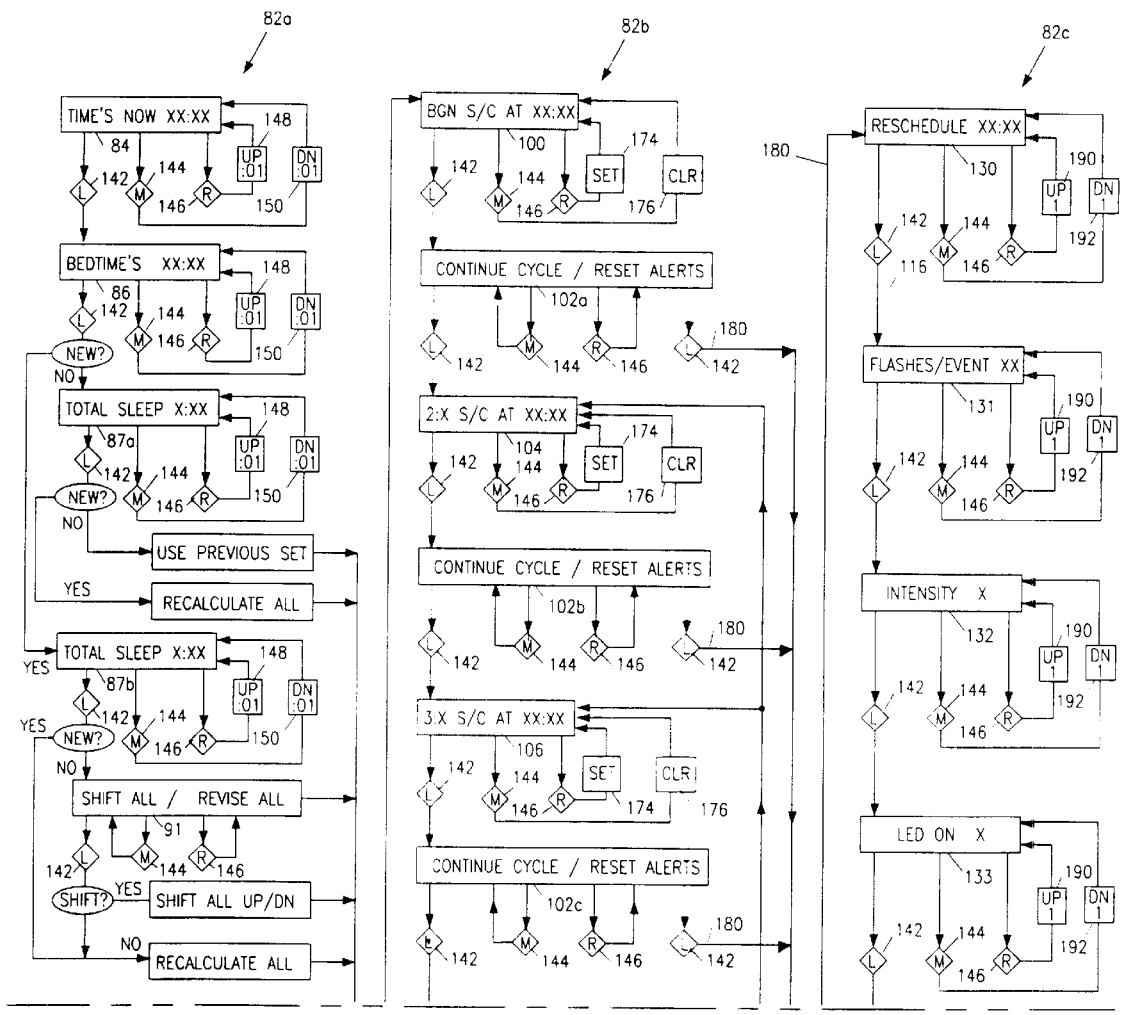
FIGS. 11a and 11b together are an operational flowchart illustrating the Program Interface as the user sets the times and alert variables for the inventive dream analyzer apparatus.
Figure 11B:
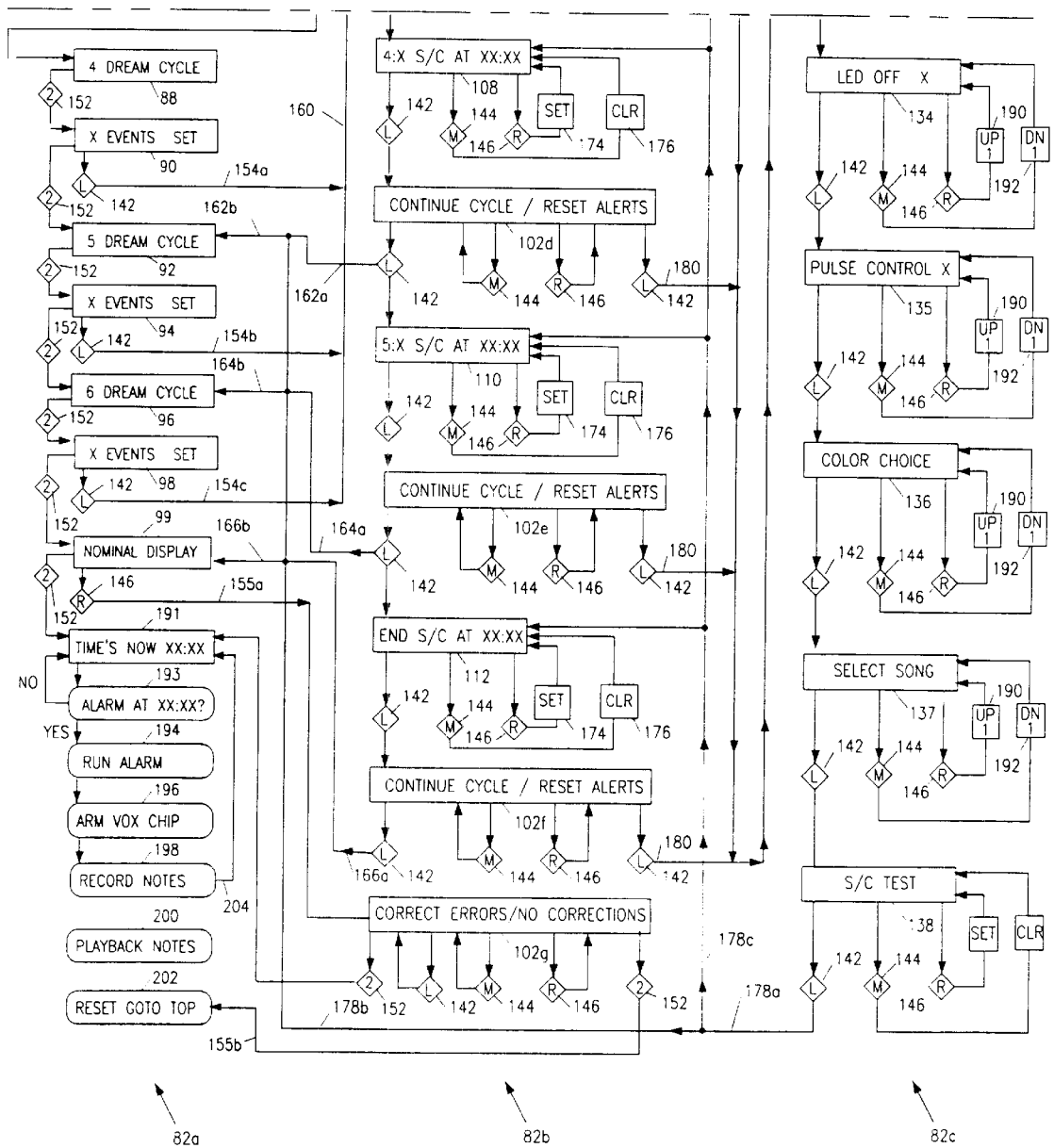

The software program running the microcontroller 60 is initialized by pressing on/off button 48a in conjunction with reset button 47a. The sequence of boxes 84, 86, 87a, 87b, 88, 90, 92, 94, 96, 98 and 99 in FIGS. 11a and 11b show the display of LCD screen 42a at each programming step. LCD screens 84, 86, 87a or 87b represent the steps of entering the user's sleep period information, which dream analyzer 18 uses to calculate the times of the alerts. The user begins the process of programming dream analyzer 18 by inputting the start time and length of his or her sleep period. Initial LCD screen 84 displays the current time "XX:XX", where "X" represents the decimal value that appears on LCD screen 42a as the result of user input or the operation of dream analyzer 18. The current time may be adjusted up 148 in one minute increments by pressing button 146 ("R"), which corresponds to right button 40a as shown in FIGS. 7 and 8.

Similarly, the time may be adjusted down 150 in one minute increments by pressing button 144 ("M"), which corresponds to middle button 38a. The user then enters the time displayed on LCD screen 84 by pressing button 142 ("L"), which corresponds to left button 36a. These same buttons 146 (40a), 144 (38a) and 142 (36a) are also used to select between the options presented in each subsequent programming step, as indicated in FIGS. 11a and 11b.

Once the current time is set, microcontroller 60 displays LCD screen 86 showing the previously stored BEDTIME value, which corresponds to the user's time for going to bed. The user may either accept or set a new BEDTIME value by pressing buttons 146 (40a), 144 (38a) and 142 (36a) as described above for setting the current time. Microcontroller 60 compares the entered BEDTIME value with the previous BEDTIME value. If the user accepts the previous BEDTIME value, microcontroller 60 displays LCD screen 87a showing the previously stored TOTAL SLEEP time, which corresponds to the total length of the user's sleep period. The user may then accept or set a new value for the TOTAL SLEEP time by pushing buttons 146 (40a), 144 (38a) and 142 (36a) as before.

If the user accepts the previous TOTAL SLEEP time displayed on LCD screen 87a, the program proceeds to review the number of events set for each alert event cycle by automatically displaying the sequence of LCD screens 88, 90, 92, 94, 96 and 98, as indicated by diamond shaped automatic sequencing blocks 152. LCD screen 88, 4 DREAM CYCLE, indicates that the number of alerts set for a sleep period having 4 REM events will be reviewed. Microcontroller 60 then automatically displays LCD screen 90, which shows the current number of programmed alerts SET for a 4 REM event cycle sleep period. The user may interrupt the automatic sequence of the program and reschedule any of the 4 REM event cycle alert times by pressing left button 142 (36a) in response to LCD screen 90.

The user may accept the previously programmed 4 REM event cycle alert times by allowing the automatic sequence of LCD screens to proceed uninterrupted. Microcontroller 60 then displays LCD screens 92 and 94, which allow the user to review and reschedule the previously programmed times for each of the alerts SET corresponding to a 5 REM event cycle sleep period, in the same manner as screens 88, 90. If the user does not interrupt LCD screen 94, microcontroller 60 automatically proceeds to display LCD screens 96 and 98, which similarly allows the user to review and reschedule the previously programmed times for each of the alerts SET corresponding to a 6 REM event cycle sleep period.

If the user accepts the previously programmed BEDTIME value shown on LCD screen 86, but enters a new TOTAL SLEEP time in response to LCD screen 87a, microcontroller 60 automatically recalculates, without setting or clearing their alert status, the predicted times for each of the 11 alerts based on the new TOTAL SLEEP time, and then proceeds to display the automatic sequence of LCD screens 88, 90, 92, 94, 96 and 98, as described above.

If the user enters a new BEDTIME value in response to LCD screen 86, the previously stored TOTAL SLEEP time is displayed on LCD screen 87b. As before, the user may accept or enter a new value for the TOTAL SLEEP time. If the user accepts the previous TOTAL SLEEP time, microcontroller 60 then displays LCD screen 91, which provides the user with the option to SHIFT ALL or REVISE ALL of the programmed times for each alert. The user selects the SHIFT ALL or REVISE ALL options by pressing middle button 144 (38a) or right button 146 (40a), respectively, and then entering the selected option by pressing left button 142 (36a).

If the user selects and enters the SHIFT ALL option, microcontroller 60 shifts all of the programmed alert times by an amount equal to the change in BEDTIME value. The SHIFT ALL option allows the user to change the BEDTIME value and preserve previous alert settings, without rescheduling each alert. Thus, the SHIFT ALL option is useful where the user has developed individualized alert settings found to be particularly effective based on previous experience and merely wishes to accommodate a change in BEDTIME.

If the user selects and enters the REVISE ALL option in response to LCD screen 91, microcontroller 60 recalculates, without setting or clearing their alert status, the predicted times for each of the 11 alerts based on the new BEDTIME value. Similarly, if the user enters a new BEDTIME value and a new TOTAL SLEEP time in response to LCD screens 86 and 87b, then microcontroller 60 recalculates, without setting or clearing their alert status, the predicted times for each of the 11 alerts based on the combination of the new TOTAL SLEEP time and the new BEDTIME values.

It will be readily apparent to one skilled in the art that microcontroller 60 can be used to calculate the TOTAL SLEEP value if the user's time to wake up is known. Thus, in an alternative embodiment, the user may input his or her "WAKE UP" time, instead of the TOTAL SLEEP time.

Once the alert times are calculated and stored, microcontroller 60 automatically sequentially displays LCD screens 88, 90, 92, 94, 96 and 98, as described above. LCD screens 88, 92 and 96 show the location of the user in the program step of reviewing the 4, 5 or 6 REM event DREAM CYCLE. LCD screens 90, 94 and 98 respectively display the number of alerts programmed for the 4, 5 and 6 DREAM CYCLE. The user may choose to allow the program to automatically sequence through LCD screens 90 to 98 without interruption, thereby accepting the settings of previous use as the settings of the present use. Microcontroller 60 then completes the programming process by automatically displaying LCD screen 99 NOMINAL DISPLAY, and then LCD screen 191 TIME'S NOW XX:XX, which displays the current time in minutes until a programmed alert occurs. This will be the usual mode as users empirically arrive at their individual settings with the use of the dream analyzer 18 over a period of time.

Should the user desire to review and/or reset the time of the alerts, he or she may interrupt the automatic sequence of LCD screens 88, 90, 92, 94, 96 and 98, and send the program to the second level of LCD screens 82b through paths 154a, 154b and 154c. The second level 82b comprises the sequence of LCD screens 100, 104, 106, 108, 110 and 112, which allow the user to review and change the status of each alert. Pressing left button 142a (36a) in response to LCD screens 90, 94 or 98 causes microcontroller 60 to display LCD screen 100, showing the time of the first alert in the appropriate DREAM CYCLE and whether it is SET ("S") 174 or CLEAR ("C") 176. At LCD screens 100, 104, 106, 108, 110 and 112, pressing the right button 146 (40a) will SET 174 an alert at the time shown, and pressing the middle button 144 (38a) will CLEAR 176 an alert so that the alert will not occur at the time shown. Pressing the left button 142 (36) enters the selected SET or CLEAR option and continues the programming sequence.

If the SET option is selected and entered, each LCD screen 100, 104, 106, 108, 110 and 112 respectively proceeds to LCD screens 102a, 102b, 102c, 102d, 102e and 102f, which provide the user with the option to CONTINUE CYCLE and review the time programmed for the next alert in the DREAM CYCLE, or RESET and reschedule the programmed alert variables. Continuing to press the left button 142 (36a) in response to LCD screens 102a, 102b, 102c, 102d, 102e and 102f will accept the default screen CONTINUE CYCLE and display the next LCD screen in the sequence. If the CLEAR option is selected and entered in response to LCD screens 100, 104, 106, 108, 110 and 112, the program skips the corresponding LCD screen 102a, 102b, 102c, 102d, 102e or 102f and proceeds to the next LCD screen in the previous sequence. This review/reset sequence will continue until the last alert in the DREAM CYCLE is displayed on either LCD screen 102d (4 DREAM CYCLE), 102e (5 DREAM CYCLE) or 102f (6 DREAM CYCLE). Pressing left button 142 (36a) at this point accepts the current alert settings and sends the program to the next step of the first level of screens 82a through paths 162a, 164a and 166a.

For example, pressing left button 142a (36a) in response to LCD screen 90 sends the program to the second level of screens 82b through path 154a, and causes microcontroller 60 to display LCD screen 100, showing the time of the first alert in the 4 DREAM CYCLE and whether it is SET 174 or CLEAR 176. The user may select the SET 174 or CLEAR 176 options by pressing either right button 146 (40a) or middle button 144 (38a), respectively, and then entering the selection by pressing left button 142a (36a). If the SET 174 option is selected, microcontroller 60 displays screen 102a, which provides the user with the option to CONTINUE CYCLE and review the subsequent alert settings or RESET ALERTS and reschedule the current alert and its variables. The CONTINUE CYCLE or RESET ALERTS options are selected by pressing either middle button 144 (38a) or right button 146 (40a), respectively, and then entered by pressing left button 142a (36a).

If the user selects the CONTINUE CYCLE option in response to LCD screen 102a or selects the CLR 176 option in response to LCD screen 100, microcontroller 60 displays LCD screen 104 showing the time of the second alert in the 4 DREAM CYCLE and whether it is SET 174 or CLEAR 176. The user may choose to SET 174 or CLEAR 176 the displayed alert time and then CONTINUE CYCLE or RESET ALERTS as before. Each of the alert times programmed in the 4 DREAM CYCLE may be sequentially reviewed and reset by proceeding through LCD screens 100, 102a, 104, 102b, 106, 102c, 108 and 102d in this manner. Pressing left button 142a (36a) in response to LCD screen 102d returns the program to the first level of screens 82b at LCD screen 92 through path 162a.

Similarly, pressing left button 142 (36a) at the last LCD screen 102e for the 5 DREAM CYCLE, returns the program to LCD screen 96 through path 164a. Pressing left button 142 (36a) at the last LCD screen 102f for the 6 DREAM CYCLE, returns the program to LCD screen 99 NOMINAL DISPLAY, through path 166a.

Selecting and entering the RESET ALERTS option in response to LCD screens 102a, 102b, 102c, 102d, 102e, or 102f, sends the program through path 180 to the third level 82c, comprising the sequence of LCD screens 130, 131, 132, 133, 134, 135, 136 and 137, which allow the user to reschedule each of the alert variables. For example, LCD screen 130 displays the time set for the alert. LCD screen 131 displays the FLASHES/EVENT value, which represents the number of times alert LEDs 54a, 56a and 58a are flashed during an alert and ranges from 0 to 29. LCD screen 132 displays the INTENSITY value, which represents the intensity of the flashes. LCD screen 133 displays the LED ON value, which represents the length of time the alert LEDs 54a, 56a and 58a are on during a flash. LCD screen 134 displays the LED OFF value, which represents the length of time between flashes. LCD screen 135 displays the PULSE CONTROL value, which represents the ramping up and down of the intensity of alert LEDs 54a, 56a and 58a during a series of flashes. The values of LCD screens 132, 133, 134 and 135 arbitrarily range from 0–9. In alternative embodiments, dream analyzer 18 may be reprogrammed to provide a larger or smaller number of intervals over the range for these variables.

LCD screens 136 and 137 have non-numerical values. LCD screen 136 displays the COLOR CHOICE value, which represents the color of the flash. By using different combinations of red 54a, green 56a and blue 58a alert LEDs, dream analyzer 18 may produce flashes that are White, Red, Yellow, Green, Blue, Blue-Green or Magenta in color. LCD screen 137 displays the SELECT SONG value, which represents the melody or other alert sound that is played during an alert. A microcontroller, such as the PIC16F876 chip, has sufficient memory space to program a dozen or more melodies, as the user may desire.

The numerical values for each alert variable displayed by LCD screens 130, 131, 132, 133, 134 and 135 may be adjusted up 190 by pressing right button 146 (40a) or down 192 by pressing middle button 144 (38a). Pressing right and middle buttons 146 (40a), 144 (38a) in response to LCD screens 136 and 137, cycles through the various COLOR CHOICE and SELECT SONG values. Once the appropriate value is selected, pressing left button 142 (36a) enters the displayed value and causes microcontroller 60 to display the next LCD screen in the sequence.

The programmed values of the alert variables are shared between certain alerts according to their relative time of occurrence during the user's sleep period. Alerts are divided into early, middle and late categories. In the 4 REM event cycle, the first two REM events are classified as early, the third is classified as middle, and the last is classified as late. In the 5 REM event cycle, the first two REM events are early, the third is middle, and the last two are late. Finally, in the 6 REM event cycle, the first two REM events are early, the second two are middle, and the last two are late.

Alerts in each category share the same alert variables, except the alert time. Thus, setting an alert variable for any early alert, other than the alert time, will set that alert variable for all early alerts in the 4, 5 and 6 DREAM CYCLEs. Similarly, except for the alert time, all alerts in the middle category share the same alert variables and all late alerts share the same alert variables. This arrangement of alert variables allows the user to store variable settings for the alerts for the early, middle or last part of the sleeping period and provides greater control over awakenings by cutting alert values to the barely noticeable during one part of the sleep period, while holding other alert values constant as a control group in dream awakening experimentation.

Although it is possible to program an alert at a time that is earlier or later than the time calculated by microcontroller 60, the alert will retain its original early, middle or late classification. For example, the time of the first alert in the 4 DREAM CYCLE may be rescheduled for the end of the sleep period, but will still retain the early alert variables.

Once all of the alert variables are programmed for the alert, pressing left button 142 (36a) in response to LCD screen 137 causes microcontroller 60 to display LCD screen 138, which allows the user to TEST the program by reviewing the sequence of alert variables and the overall effect of the sounds and lights programmed for each alert. Pressing right and middle buttons 146 (40a), 144 (38a) in response to LCD screen 138, respectively selects between the default CLR TEST option to skip the test, and the SET TEST option to run the TEST. If the user makes no selection, the default value is CLR TEST. The selection is then entered by pressing left button 142 (36a). A selection of SET TEST or CLR TEST is operative unless changed later in the programming or unless the device program is reset which reestablishes the default setting of CLR TEST.

If the SET TEST option is chosen, dream analyzer 18 will display LCD screen 191, but will pass time at the rate of 4 minutes per second until a programmed alert occurs. The TEST will then play the flashing LEDs and alert sounds comprising the programmed alert variables at the normal rate of time. Once the alert is completed, dream analyzer 18 resumes passing the time at the accelerated rate. The TEST proceeds through a 12-hour period in this fashion, playing each programmed alert until device reset button 47a is pressed to clear the TEST and reset the program.

Dream analyzer 18 does not store the time displayed during a TEST. After the TEST is completed and the user resets the device, the program returns to LCD screen 84 which shows the actual current time. The user may then proceed from the LCD screen 84 to LCD screen 191 by pressing the left button 142a (36a) to progress through LCD screens 84, 86 and 87a without changing any of the input values, and then allowing the program to automatically proceed through the remaining steps without further button press, as described above.

If the user accepts the default CLR TEST option, the program returns to the next sequential program step in the first level of screens 82a along path 178a to 178b or the second level of screens 82b along path 178a to 178c or if at the end of the 6 EVENT CYCLE proceeds to the final user input screen 99, NOMINAL DISPLAY.

All user data in the microcontroller is stored in a separate bank called EEPROM (Electrically Erasable Programmable Memory) (not shown), which will retain all user data even when the device is without power. However, the stored user data may become corrupted in conditions of low power or static discharge. This condition may be resolved by pressing right button 146 (40a) at LCD screen 99 NOMINAL DISPLAY, which allows the user to return the program to the LCD screen 84 to reconfigure the user data. The use of the right button 146 (40a) to reprogram the user data at LCD screen 99, rather than the usual left button 142 (36a), which is used to interrupt the automatic sequencing of screens, helps to prevent accidental reset by the user.

Pressing right button 146 (40a) at LCD screen 99 NOMINAL DISPLAY, causes microcontroller to display LCD screen 102g, which provides the user with the option to CORRECT ERRORS and reprogram the user data, or to enter NO CORRECTIONS. Pressing right button 146 (40a) at LCD screen 102g selects the CORRECT ERRORS option and causes the EEPROM memory bank to be cleared via path 155b. A blank LCD screen is then displayed to indicate that the reprogramming has taken place and that the device must be reinitialized and programmed with all new entries made by the user beginning at LCD screen 84, as previously described. Pressing either middle button 144 (38a) or left button 142 (36a) returns the program to its normal progression and displays LCD screen 191, showing the current time. If the user does not press either right, middle or left buttons 146 (40a), 144 (38a) or 142 (36a), the program will proceed automatically from LCD screen 102g to LCD screen 191.

In addition, pressing the device on-off button 48a and then the device reset button 47a at any time will also restart the program at LCD screen 84, as indicated by operational step 202.

Once the user has input his or her sleep period information and completes the programming of dream analyzer 18, microcontroller 60 displays the current time on LCD screen 191 and proceeds with operational steps 193, 194, 196 and 198. As previously mentioned, oscillator 62b is used as a watch crystal, which provides input to the timer function of microcontroller 60. In the case of a PIC16F876 chip, the Timer 1 function is a 16 bit register which counts up until it rolls over at zero and sets an interrupt bit. The timer is two seconds long with the default loading, but in the preferred embodiment is loaded halfway to produce a rollover each second. The PIC16F876 chip is ordered to sleep each second and only reawakens with the Timer 1 interrupt. It then will increase that minute's seconds, increase the display by one minute when required, store the new time as each minute is increased, check whether an alert has been programmed for that time 193, play an alert if appropriate, and then returns to sleep. The oscillator 62b thereby provides electronic unit 30 with an accuracy of within a few seconds per day. The timing interrupt is continuous through user programming, running the alert sequences and keeping clock time. If electronic unit 30 loses power or is otherwise reset, it will, when restarted, display the stored value when power down occurred.

If it is determined in step 193 that an alert has been programmed for the current time, then microcontroller 60 will play the alert 194 if the alert has been set or bypass the alert if cleared. As indicated by step 196, during an alert LCD screen backlight 43 is turned on and voice activated switch 64 is enabled for a period of approximately 15 minutes after the end of the flashing light and/or sound alert. During this 15 minute period, voice recording/playback chip 66 will record the user's spoken description of his or her dream, as shown by step 198. Alert LED 61a is turned on only while recording is actually taking place. If the user is not awakened, voice recording/playback chip 66 will not record and, after the 15 minute period, LCD screen backlight 43 and voice activated switch 64 are turned off until the next set alert. In the morning, the user may playback any recordings made during the previous night, which will be a continuous message.

Voice recording/playback chip 66 automatically resets for the next alert and begins a continuous record over any notes made previously. The user may also manually playback or record by pressing playback/record button 52a in conjunction with voice chip reset button 53a and chip enable button 55a. Accordingly, the user may manually enable the recording and playback modes at any time other than the programmed alert times enabled by the microcontroller 60.

Figure 13:
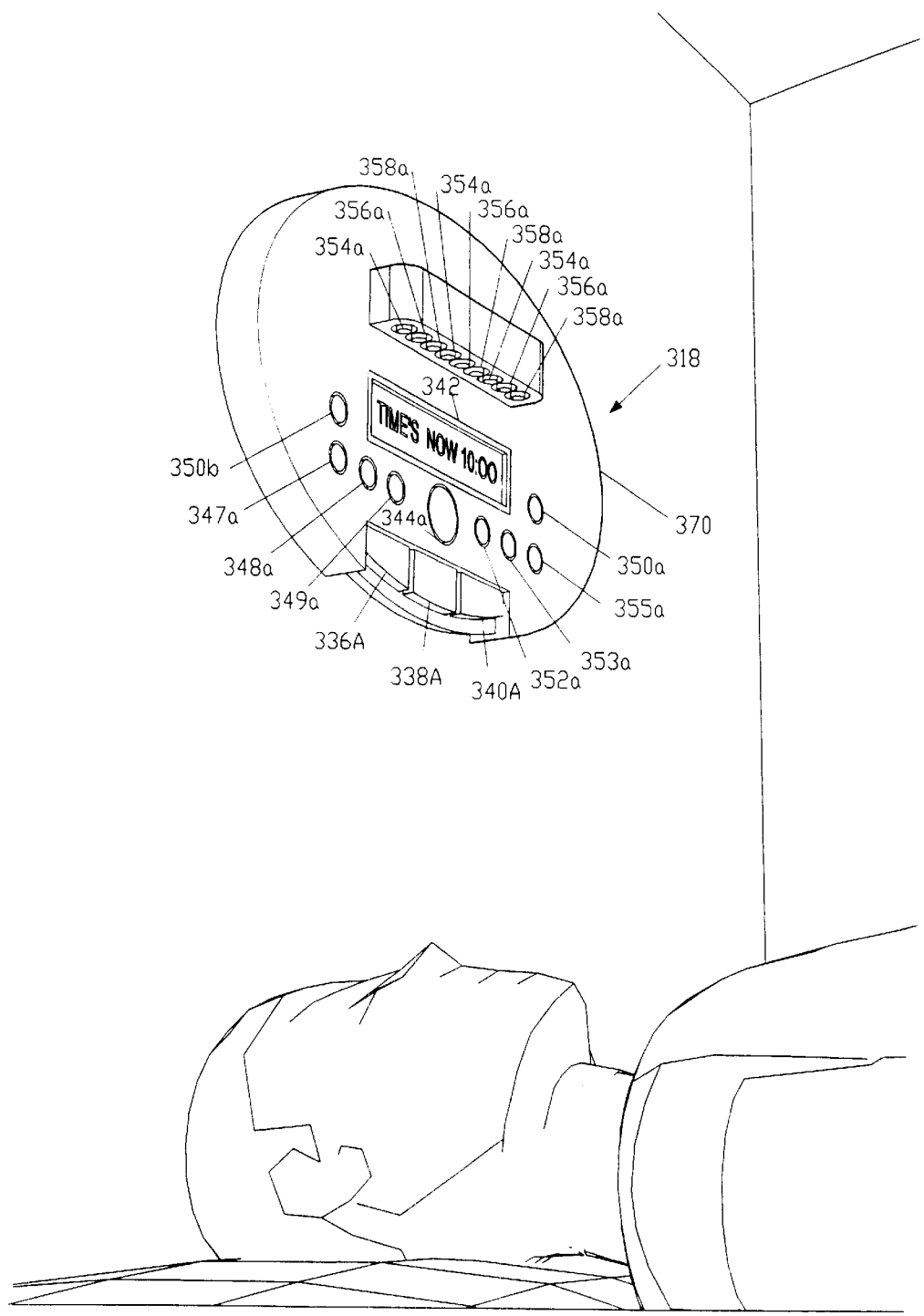
FIG. 13 is a perspective view of an alternative embodiment of the inventive dream analyzer apparatus, shown in relation to the user.

FIG. 13 shows an alternative embodiment 318 of the present invention, which is housed in a one-piece casing 370. Dream analyzer 318 provides the same features shown in the preferred embodiment, described above. Red 354a, green 356a and blue 358a LEDs are shown in the same orientation as in the preferred embodiment. However, the speaker 344a, the electret microphones 350a and 350b, the LCD screen 342a, the left, middle and right pushbuttons 336a, 338a and 340a, the device reset button 347a, the device on/off button 348a, the alert sound volume button 349a, the Sound Playback button 352a are all at right angles to the orientation of the preferred embodiment.

All features and operations of the preferred embodiment are the same as those of the alternative embodiment. The significant differences between the two are the removable electronic unit 330 of the preferred embodiment shown in FIG. 7. This is smaller than the assembly 318 of FIG. 13 and is easy to remove from its normal placement and its orientation is both more accessible and readable than the alternative embodiment.

Dream analyzer 318 may have the advantage of lower cost through the use of less casing, tooling and material. In addition, dream analyzer 318 may have an aesthetic advantage in that it is similar to a picture mounted to the wall and, therefore, may be more familiar to the user.

In a further embodiment of the present invention, the dream analyzer apparatus includes an input/output plug or jack for connection to a computer port or sound card, as is well known in the art. The user's oral recordings can then be converted and stored as text, using commercially available software such as "Naturally Speaking 5.0" by Dragon Systems, Inc. In addition, the computer can be used to transmit the user's oral or text records via the Internet, to facilitate analysis or share information with others on a web site. Conversely, be enabling direct reprogramming of microcontroller 60, the computer may be used to download material to dream analyzer 18 from the Internet, computers or similar devices, such as alert variable settings, program upgrades or additional alert sounds.

While my above descriptions contain many specificities, those should not be construed as limitations on the scope of the invention, but rather as exemplification of one preferred embodiment thereof. Many other variations are possible. For example: cell phone, personal digital assistant and hand-held electronic game operations could also easily adopt the means herein disclosed. Accordingly, the scope of the invention should be determined not by the embodiments illustrated, but by the appended claims and their legal equivalents.

Appendix A

```
     :0200000087284F
     :0800080083168C0183120B1317
     :100010008B130C101010F600030E8301F7000A0872
 5   :100020008A01F80029306E02031D25280A160020D7
     :100030000A1283168030860006309F00003085004B
     :10004000831220308500303086007F1C3A288B1CBC
     :100050002E280230CA00051E35283A2800304A02F0
     :1000600000031939228CA030B163A28051A3A28CB0176
10   :100070003A284B148B100C10101000300F02031D87
     :100080004A2880308F000C308E00F40B4A28F30A87
     :100090003C30F40074083C3C031C482883168C0157
     :1000A0000C1483128C01101478088A00770E8300D8
     :1000B000F60E760E8B100B170900820702341E34E1
15   :1000C0003A34563472348E34AA34C634E234FD34B1
     :1000D000003400340034003400340C340C340C345C
     :1000E0000C341734173417348207003403340634C1
     :1000F00009340C340E341234153419341C3482078C
     :100100000E340234063404340C3408340A34E10169
20   :100110000A128A1500208A15F301F401D301D201D5
     :10012000D101A20125142614E901C501831600306E
     :10013000870001C30860006309F003E308500831209
     :100140000030870000308500BC3086000B138B1315
     :1001500083120313C10101080308F000C308E00AF
25   :100160002D30F40083168C010C1483128C010B17B4
     :100170000E30900010140A128A155D268A11E727A6
     :10018000B30C500CF272230EE00F027CF270130FB
     :100190002002031294C292230EE0051210A30EE00D2
     :1001A0007F210130EE00B8210230EE0090220000E5
30   :1001B0008B138A1576218A1128306F020319DF28E4
     :1001C0008B17F30183163E3085000C3086008312B6
     :1001D00000030850020308600000006030860000007E
     :1001E000203086004C2900000030EF000F30EE0078
     :1001F000F027CF270130FD00CE256F08013C031901
35   :10020000002290800E901A7011E30EE00F02755255C
     :100210006021432555250C252E08EF0061253C253E
     :10022000CF270330EE001E24CF271E24A701043061
     :10023000EE002D24CF272D24CF27A7010530EE0077
     :100240003C24CF273C24CF27A7010630EE004B24C7
40   :10025000CF274B24CF27A7010730EE005A24CF2702
     :100260005A24A7010830EE006924CF276924CF273C
     :10027000A7012A30EE00F0278B130A16F7200A1286
     :100280008B17CF27A7010930EE009124CF27080054
     :100290004508F000A826C3280E30EE00F027E72717
45   :1002A00048290530F0006021432555250C252E08EE
```

```
     :1002B000EF0061253C25CF2725142230EE000800F1
     :1002C000B6244325DD2499276F08AE0005250800D4
     :1002D000B6244325A0276F08C100A0276F08C000DF
     :1002E000A0276F08AF00A0276F08AE000525080003
   5 :1002F000432514252E08EF0061253C250800F02732
     :10030000E7270B30F00060214208FC00C4004308DE
     :10031000FB00CC00432555250C252E08EF00612558
     :100320003C25CF27C60142084402031D9B294308F0
     :100330004C02031908000130CE00C6007B08F10012
  10 :100340003230F000B027CF277C08F1001B30F000DE
     :10035000B027CF2729144030EC0029148B138A15BD
     :1003600051218A118B1729103930F00078210800AB
     :10037000F027E7271030F000B6244325DD240525BB
     :100380004208C4004308CC0043257008053EF00035
  15 :1003900028140C253C25CF27A80142084402031D40
     :1003A000DA2943084C02031DDA294608003C0319E8
     :1003B0000800E1294E14FB25251427140130EE0016
     :1003C00008000B30F00068217D102430EE00F0278B
     :1003D000CE25FD016E08243C0319FF290130CE0013
  20 :1003E0004308FB00F1003230F000B027CF2742086D
     :1003F000FC00F1001B30F000B027CF270B2A0030A3
     :10040000CE003230F000A527FB00CF271B30F000D4
     :10041000A527FC00142A4030EC0029148B138A1500
     :1004200051218A118B1729103930F0004E1C2D22D2
  25 :100430001F22FB25251427142230EE0008004E1839
     :100440002B2A682154227E08E700B62499265525D8
     :10045000393070020 31D78210800FA01FE01F9010C
     :100460000C30E7007C086702EB000C304202EB071F
     :100470006B080318402AF9007908003CF900412A6A
  30 :10048000FA0000003C30E7007B086702EB003C30DC
     :100490004302EB070318512A6B08003C3C3CEB007D
     :1004A000F90A6B08FE0008007A08C4004408003C02
     :1004B0000319612A42080C3C0319C201C20AC40391
     :1004C000562A7908C4004408003C0319722A4208DD
  35 :1004D000013C03196E2AC403C203632A0C30C20014
     :1004E000C403632A42080C3C0319822A42080B3CCD
     :1004F0000319872A42080A3C03198B2AAE014208D5
     :10050000AF008E2A0130AE000230AF008E2A0130DB
     :10051000AE00AF008E2A0130AE00AF017E080800A9
  40 :10052000F027E72743250430EF00DB22E1223330B8
     :10053000F000F522E622EE22003C03194B2BD522D7
     :100540000530EF00DB22E1223330F000D001FB2246
     :100550004F30F000FB22FB22FB224830F000A527A1
     :10056000D007E622EE22003C0319842BD522063068
  45 :10057000EF00DB22E1223330F000D001FB226430B7
     :10058000F000FB22FB22FB22FB224830F000A527D3
```

```
:10059000D007E622EE22003C0319CA2B69106A1428
:1005A000251027140230EE0008000230EE00F0277C
:1005B000E727432508003130ED00F027D827D8275A
:1005C00008002330EE00F027E72708005008EF006E
:1005D00043253130ED00F027E72708000130EA001D
:1005E000D827691468256A080800D001FB22FB227D
:1005F000FB22FB220800A527D00759250800432528
:10060000DD2499276F08AE000525A5276A14013C53
:100610003191112B7008A4001530EE00F027E7270E
:10062000172B7008A4001630EE00F027E727682586
:100630006A08013C0319172B2408F0006E08163CC9
:100640000319282B0030F100B027F027E727080016
:100650000130F100B027F027E72708003930F0001B
:10066000030D40008002130EE00F027CF2708002A
:10067000EE00F027CF2708006A146914FF22EA0170
:10068000E9010800F000A527013C08004E30F00009
:100690001730D400080033231130382339 30F000EC
:1006A000030D4003C23333042230319F320D827F1
:1006B0003323123038231730382340 30F000003015
:1006C000D4003C233A3042230319F320D8273323A4
:1006D00012303823183038234730F0000C30D40063
:1006E0003C23413042230319F320D8273323 1F3002
:1006F000EE00F027CF2746233C2348304223 03193E
:10070000F320D827E9019F2A3323113038 2339 30C9
:10071000F0000030D4003C2333304223 0319F3208F
:10072000D8273323 13303823173038 235530F000BF
:10073000000030D4003C234F3042230319F320D82744
:100740003323 13303823183038 235C30F0000C305A
:10075000D4003C23563042230319F320D8273323F7
:1007600013303823193038 236330F0000C30D400B4
:100770003C235D3042230319F320D8273323 1F3055
:100780000382346233C2348304223 0319F320D8273B
:10079000E901B62A3323 1130382339 30F000003014
:1007A000D4003C23333042230319F320D8273323CA
:1007B0001430382317303823 6A30F0000030D4006A
:1007C0003C237F3042230319F320D8273323 1430EE
:1007D00038231830382371 30F0000C30D4003C231B
:1007E0006B3042230319F320D82733231430 3823E6
:1007F000193038237830F0000C30D4003C237230AC
:100800004223 0319F320D8273323 14303823 1A3016
:1008100038237F30F0001730D4003C2342230319E3
:10082000F320D8273323 1F30382346233C23483076
:1008300042230319F320D827E901D22AF027CF2732
:100840004825 13305407F000BF24E72451251E2506
:100850002514271403 30EE000800F027CF2748258 1
:1008600016305407F000C824F3244D251E25251406
```

```
:1008700027140430EE000800F027CF274825173052
:100880005407F000C824F3244D25302525142714DF
:100890000530EE000800F027CF2748251830540710
:1008A000F000C824F3244D253025251427140630E4
:1008B000EE000800F027CF27482519305407F00034
:1008C000C824F3244D253025251427140730EE00C5
:1008D0000800F027CF270B30EE003F30ED001A3034
:1008E0005407F000CF27C8240630AC00AD0001301B
:1008F000A200F92400302702031D882C8B138A15CF
:100900001A208A118B17FA242208013C03197E2C25
:100910004D254108EF006125251427140830EE000D
:100920000800F027CF276A1469142608013C031930
:100930009E2C1630EE00F027E727A52C1530EE0090
:1009400F027E7270130F100A92C0130A700F101C1
:10095000CF2768257108A6006A08013C0319A92C55
:10096000E901251427140930EE0008000930AC0015
:100970000530AB000930AA003C30AD00080009305A
:10098000AC000230AB000030AA001E30AD00080001
:100990000030AB00AA000930AC00AD000800A02771
:1009A0006F08C100A0276F08C000A0276F08AF0024
:1009B000A0276F08AE000525080099276F08C10021
:1009C00099276F08C00099276F08AF000800992782
:1009D0006F08C10099276F08C000A0276F08C300E7
:1009E0003F30ED00080099276F08C1003F30ED004F
:1009F0000800A0278B130A128A1508268A118B1764
:100A00006F08C1003F30ED000800A0276F08C30049
:100A1000A0276F08C200080027088B138A15003C26
:100A20003191A208A118B174108EF00612540082D
:100A3000EF0061252F08EF006125080027088B13C0
:100A40008A15003C03191A208A118B174108EF0000
:100A500061254008EF0061254308EF00612508008B
:100A600027088B138A15003C03191A208A118B174B
:100A70004108EF00612508004308EF0061254208A6
:100A8000EF00612508000E30EE003F30ED00080059
:100A90000D30EE003F30ED0008007008013EF00020
:100AA00008007008033EF00008007008063EF000E1
:100AB00008007008073EF000080070080D3EF000C6
:100AC00008006F08F100B027E727ED03F0030800E6
:100AD0008614061586150616861005330E200FF30CE
:100AE000E4008F30E300061D802D861D892D061E33
:100AF000A42DE30B732DE40B712DE20B6F2D080079
:100B0000CF276908013C0319872D271008006A10B8
:100B100800CF276908013C03198F2D08006E08D3
:100B2000153C03199D2D6E08163C03199D2D6B086D
:100B3000F0000130F100B02708001530EE00F0277A
:100B40000130F1006A140800CF276908013C03193D
```

34

```
      :100B5000B32D2608003C0319C72D0030A6001C3019
      :100B6000EE00F02708006E08153C0319C12D6E0831
      :100B7000163C0319C12D6B08F0000030F100B027BE
      :100B800008001630EE00F027F1016A140800013069
 5    :100B9000A6001D30EE00F027CF27080086140615AA
      :100BA000861506168610061DDA2D861DDB2D061EFF
      :100BB000EB2DD32D08007D1CE62D0030EF000F300B
      :100BC000EE00F027CF270030CE00D32D2430EE00EA
      :100BD000F027CF27D32D7D1CF62D0130EF001030EC
10    :100BE000EE00F027CF270130CE00D32D2530EE00C8
      :100BF000F027CF27D32D4E1C372E27141030F000AE
      :100C00004325A0276F08C100A0276F08C000A027B8
      :100C10006F08AF0005252F08E7000630E7026708D8
      :100C2000003C03191F2E6708013C0319212E670899
15    :100C3000023C0319242E6708033C0319272E43089E
      :100C4000292E43083C3E292E4308783E292E43088E
      :100C5000B43EEB00E800E701E70A0330EB020318BB
      :100C60002C2E5630E7073930F000682199264030A5
      :100C7000F0001F224E1C3F2E0730E7079926473011
20    :100C8000F0001F224E1C472E0730E70799264E30F2
      :100C9000F0001F224E1C5A2E6808EB00E701E70AFD
      :100CA0000430EB0203184F2E3E30E7073930F000D6
      :100CB000682199265530F0001F224E1C622E053007
      :100CC000E70799265C30F0001F224E1C6A2E053083
25    :100CD000E70799266330F0001F224E1C7D2E68081E
      :100CE000EB00E701E70A0530EB020318722E2F3004
      :100CF000E7073930F000682199266A30F0001F229A
      :100D00004E1C852E0430E70799267130F0001F2213
      :100D10004E1C8D2E0430E70799267830F0001F22F4
30    :100D20004E1C952E0430E70799267F30F0001F22D5
      :100D300008006708EC0029148B138A1551218A11C9
      :100D40008B17291008002508003C0319A826080065
      :100D50002230EE00F027E7270E30EE00E7272510BF
      :100D60004508F0000B3C031DB72E0530F000A00134
35    :100D7000B6244325DD2499276F08AE0005254325B9
      :100D800055258B138A1534288A118B172608003CA9
      :100D90000319D62E26276D08C6000530F00014254D
      :100DA0002E08EF0061253C254608ED00DC260130C9
      :100DB000200203190800C12E3330D100F126F62697
40    :100DC0000013020020319080007301D07F126F6266A
      :100DD0000013020020319080051087930C031908006A
      :100DE000E42E510AD200520AD30008005208F00043
      :100DF000A5274202031D08005308F000A52743025F
      :100E0000031D08005108F000A527003C0319080045
45    :100E10008A15E9218A110A1622210A12B0308600A9
      :100E2000CF27FC308600CF27A0308600CF276E0862
```

|     |                                               |
| --- | --------------------------------------------- |
|     | :100E3000E7002930EE000000630000006708EE00C4   |
|     | :100E40006E2F2230EE00F027D82708007F1C3D2FA0   |
|     | :100E500083162B0883124B02031D6327851E4E2F1A   |
|     | :100E6000CA18051A342F63274B18051E3D2F003072   |
| 5   | :100E70008600E72730308600E72700006300000087   |
|     | :100E800000030730203 19262FF30300305602031DAE |
|     | :100E9000D6030030560203194E2F08007F1C0800AD   |
|     | :100EA000FF018316AB013E3085000C3086008312B3   |
|     | :100EB0000030850020308600000060308600000091   |
| 10  | :100EC0002030860008000030 8600E727303086009A  |
|     | :100ED000E7274B088316AB008312080011305 40734  |
|     | :100EE000F000A527A000FF30D30016305407F00013   |
|     | :100EF000A527E7005D20D200D30267087420CC004C   |
|     | :100F000017305407F000A5275D20C800E100F00A63   |
| 15  | :100F1000A5275D20C900F00AA527CF00CE00F00A62   |
|     | :100F2000A5277F20D500A1012114CD018A15242AEF   |
|     | :100F30008A11A527EF00F027CF27ED03F003080063   |
|     | :100F4000A527EF00ED03F0030800700803178312D4   |
|     | :100F50008D0083168C130C1483120C0803130800E5   |
| 20  | :100F60001010700803178312700088D0071080317A2  |
|     | :100F70008C0083168C130C158B138B140B165530A9   |
|     | :100F80008D00AA308D008C148B1363000C1183121A   |
|     | :100F900003138B018B170B170000101408 00FF3090  |
|     | :100FA000E400FF30E300E30BD32FE40BD12F080064   |
| 25  | :100FB0000430E200FF30E400FF30E300E30BDE2FFB   |
|     | :100FC000E40BDC2FE20BDA2F08000A30E82F29307F   |
|     | :100FD000E6002A30E500E50BEB2FE60BE92F0800D1   |
|     | :0E0FE0008B130A128A1526258A118B1708001A       |
|     | :10100000EA01E701EB01ED01F001EC01E301E4018C   |
| 30  | :10101000E201A801A901A501A601A701E901A0011A   |
|     | :10102000A101CD01CC01CE01CF01C601FD01D60148   |
|     | :10103000EE01080086140615861506168610061D94   |
|     | :101040002628861D2828061E34281F28A2010800ED   |
|     | :1010500056210030430203190B21C3030030410223   |
| 35  | :1010600003197928C10344285621C30A2D084302D5   |
|     | :101070000319082141082C0203195F28C10A013015   |
|     | :10108000290203195129442841 08EF002625003080  |
|     | :101090002502031954296E080B3C031908001F2868   |
|     | :1010A0004008EF00ED032625ED0ACC27003025028D   |
| 40  | :1010B000031954296E080B3C031908001F2800303F   |
|     | :1010C000EF00C10001302902031 96F2826256E08A0  |
|     | :1010D0000B3C03190800003 02B0203191F2840089D  |
|     | :1010E0002B0203198B28C00A013029020319512948   |
|     | :1010F00050282C08C100EF0026256E080B3C031970   |
| 45  | :10110000080000302B0203191F284008003C031977   |
|     | :10111000B228C00350280030EF00C000013029027F   |

```
       :1011200003199928ED032625ED0A00302A02031938
       :101130001F2842080C3C03190E290130280203190C
       :101140002E292F082A020319D028C20AAF0A01301B
       :10115000290203195I292F0864210030250203199F
    5  :1011600054291F282B08EF00C000ED032625ED0AA7
       :101170000003 02A0203191F280130280203194629CA
       :101180002F08003C0319F428C203AF03642142086E
       :10119000003C03193929003025020319542 91F285E
       :1011A000C20A0030EF00AF00013029020319E12824
   10  :1011B000ED03ED032625ED0AED0A0130280203199F
       :1011C0001F28AE0A01302902031951296C21420857
       :1011D0000C3C03190E290130290203195129003052
       :1011E0002502031954291F28C2032A08EF00AF0063
       :1011F000ED03ED032625ED0AED0A0130280203195F
   15  :101200001F28AE036C214208003C031939291F280E
       :101210000030C30008002D08C30008000130C200E0
       :101220000130AF00EF00ED03ED0301302902031997
       :101230001A292625ED030030AE00EF000130290207
       :101240000003192329262 53F30ED000030250203191C
   20  :101250000542 9013029020319 51291F2809302F026E
       :1012600000 31DA1280630C200AF005F21ED0AED0A80
       :101270001F280C30C2000230AF005F21ED030130A7
       :10128000AE00EF0026253F30ED001F2806302F026C
       :10129000 0031DC0280930C200AF005F21ED0AED0A2E
   25  :1012A0001F28EC0B352808008A11C42EFF30E400FB
       :1012B000FF30E300E30B5A29E40B58290800EF0044
       :1012C000ED03ED03262508002F08EF00ED03ED03E5
       :1012D0002625ED0AED0A08002E08EF00ED03ED03C8
       :1012E000ED032625ED0AED0AED0A08002630EE0092
   30  :1012F000EF002625C62128306E02031D08000030AD
       :101300000831203178D008C00AE2103178D0A03137F
       :10131000AE21CC2703170D0803137F3C031D85293D
       :1013200003178D0108308C000313AE21A821CC27B0
       :1013300003170D0803130C3C031D962903178D0A90
   35  :101340008D0A0313AE21CC274227D72FCC270800C4
       :10135000033003178D070313AE2108001010031785
       :101360000831283168C130C158B138B140B165530AC
       :101370008D00AA308D008C148B1363000C11831226
       :1013800003138B018B170B17101408008614061516
   40  :101390008615061686100530E200FF30E4008F3017
       :1013A000E300061DDE29861DDF29061EE429E30B66
       :1013B000D129E40BCF29E20BCD290800CB29273016
       :1013C000EE00EF002625CB292830EE00EF00262581
       :1013D000CB290B3045020319192A5108063EC500D6
   45  :1013E000F0007008403C03191B2A7008553C031993
       :1013F0001B2A70086A3C03191B2A7008473C031912
```

```
     :101400001E2A70085C3C03191E2A7008713C0319DF
     :101410001E2A7008783C03191E2A70084E3C0319D6
     :10142000212A7008633C0319212A70087F3C0319A4
     :10143000212A3930C5000030D40008000C30D40017
  5  :101440000080001730D40008004F08003C0319CC01F5
     :1014500000030210203192E2A550885005208E200A7
     :101460005A22203085005308E2005A22E10B282A34
     :10147000662A2008003C03193E2A282AA1010E30C2
     :10148000D6000130A0008316AB008312FF00831644
 10  :10149000AB0006309F003030850001308600831298B
     :1014A00000030850087007030860000030308600F4
     :1014B0008A11212F00000230E4000330E300E30B27
     :1014C0005F2AE40B5D2AE20B5B2A08000130210024F
     :1014D00003196E2A4808E1002114392A4908E1005D
 15  :1014E000A0032110E10300304D020319802A4C08AB
     :1014F000D207D302CE0B392A4F08CE004D10392A1D
     :101500004C08D202D307CE0B392A4F08CE004D1417
     :10151000392A4430B3005230B4004530B500413070
     :10152000B6004D30B7002030B8004330B900593014
     :10153000BA004330BB004C30BC004530BD00080051
 20  :101540005430B0004930B1004D30B2004530B300E6
     :101550006030B4005330B5004E30B7004F30B800A3
     :101560005730B9003A30BD0008004230B100453074
     :10157000B2004430B3005430B4004930B5004D30AF
 25  :10158000B6004530B7006030B8005330B9003A308B
     :10159000BD0008005430B0004F30B1005430B200EC
     :1015A0004130B3004C30B4005330B6004C30B7007B
     :1015B0004530B8004530B9005030BA003A30BD006F
     :1015C00008004530B3005630B4004530B5004E3009
 30  :1015D000B6005430B7005330B8002030B900203086
     :1015E000BA005330BB004530BC005430BD00080089
     :1015F0004130B8005430B9002030BA003A30BD0054
     :10160000008004230B0004730B1004E30B200080050
     :101610003230B0003A30B10008003330B0003A3018
 35  :10162000B10008003430B0003A30B1000800353065
     :10163000B0003A30B10008003430B2000800353054
     :10164000B20008003630B20008004530B0004E301D
     :10165000B1004430B20008004330B4004C30B50053
     :101660005230B60008005330B4004530B500543055
 40  :10167000B60008002030B4002030B5002030B6009D
     :1016800008004530B0004E30B1004430B200080000
     :101690004630B0004C30B1004130B2005330B3009E
     :1016A0004830B4004530B5005330B6002F30B70095
     :1016B0004530B8005630B9004530BA004E30BB0056
 45  :1016C0005430BC0008002030B0004330B1004F302F
     :1016D000B2004E30B3005430B4004930B5004E3043
```

```
:1016E000B6005530B7004530B8002030B90043305F
:1016F000BA005930BB004330BC004C30BD0045300F
:10170000BE002030BF0008002030B0002030B10003
:101710005230B2004530B3005330B4004530B5000C
:101720005430B6002030B7004130B8004C30B9001A
:101730004530BA005230BB005430BC002030BD00F0
:101740002030BE002030BF0008002030B0005330F1
:10175000B1004330B2004830B3004530B4004430EB
:10176000B5005530B6004C30B7004530B8004430B5
:10177000B9002030BA002030BB002030BC003A3025
:10178000BD002030BE002030BF0008002030B00077
:101790002030B1005330B2004630B3004930B400BD
:1017A0004630B5005430B6002030B7005330B80092
:1017B0004530B9005430BA005430BB004930BC0049
:1017C0004E30BD004730BE005330BF00080020300F
:1017D000B0005230B1004530B2005630B30049304D
:1017E000B4005330B5004530B6002030B700533058
:1017F000B8004530B9005430BA005430BB0049300D
:10180000BC004E30BD004730BE005330BF00080062
:101810004C30B0004530B1004430B2004930B40023
:101820004E30B5005430B6004530B7004E30B800E9
:101830005330B9004930BA005430BB005930BC00B5
:1018400008004C30B0004530B1004430B2004F3099
:10185000B4004E30B5005430B7004930B8004D30B8
:10186000B9004530BA0008004C30B0004530B10036
:101870004430B2004F30B4004630B5004630B600B8
:101880005430B8004930B9004D30BA004530BB0083
:1018900008005030B0005530B1004C30B200533029
:1018A000B3004530B4004330B6004F30B7004E307F
:1018B000B8005430B9005230BA004F30BB004C3041
:1018C000BC0008004330B0004F30B1004C30B200D3
:1018D0004F30B3005230B40008005430B8004530E7
:1018E000B9005330BA005430BB0008005230B60083
:1018F0004530B7004430B80008005930B6004530D4
:10190000B7004C30B8004C30B9004F30BA005730F7
:10191000BB0008004730B6005230B7004530B80071
:101920004530B9004E30BA0008004230B6004C30A5
:10193000B7005530B8004530B9002D30BA004730F7
:10194000BB005230BC004530BD004530BE004E30BB
:10195000BF0008004230B6004C30B7005530B80028
:101960004530B90008004D30B6004130B7004730 6F
:10197000B8004530B9004E30BA005430BB00413099
:10198000BC0008005730B6004830B7004930B800F6
:101990005430B9004530BA0008004E30B0004F3026
:1019A000B1004D30B2004930B3004E30B400413088
:1019B000B5004C30B6002030B7004430B800493094
```

```
:1019C000B9005330BA005030BB004C30BC0041303D
:1019D000BD005930BE0008004E30B0004F30B1009D
:1019E0002030B2004330B3004F30B4005230B50065
:1019F0005230B6004530B7004330B8005430B9001B
:101A00004930BA004F30BB004E30BC005330BD00EF
:101A100008004330B0004F30B1005230B2005230B5
:101A2000B3004530B4004330B5005430B600203028
:101A3000B7004530B8005230B9005230BA004F30CC
:101A4000BB005230BC005330BD0008006E08003CA3
:101A5000031900006E08013C031960266E08023C61
:101A60000031975266E08033C0319C9266E08043C49
:101A70000000319CE266E08053C0319D3266E08063CD2
:101A80000000319D8266E08073C0319DD266E08083CAA
:101A90000000319E2266E08093C0319E7266E080A3C82
:101AA00000003195A266E080B3C00006E080C3C031903
:101AB00075266E080D3C0319F9266E080E3C0319B5
:101AC0000A2F6E080F3C0319C02E6E08103C031934
:101AD000C32E6E08113C031978266E08123C0319B8
:101AE0007D266E08133C03198C266E08143C0319DE
:101AF00091266E08153C031996266E08163C0319AC
:101B000009A266E08173C0319A6266E08183C03197E
:101B1000AA266E08193C0319AE266E081A3C031952
:101B2000B2266E081B3C0319B6266E081C3C03192E
:101B300082266E081D3C031987266E081E3C031979
:101B4000C6266E081F3C0319BB266E08203C0319ED
:101B50009E266E08213C0319A2266E08223C03191A
:101B6000502E6E08233C031970266E08243C03197E
:101B7000064266E08253C031967266E08263C031967
:101B80000F0266E08273C0319F3266E08283C03193B
:101B90000F6266E082A3C0319D3256E082B3C031940
:101BA000DA25080008000A168A1190210A128A15FF
:101BB0005621D72F42276F08003C0319EA2D6F08E2
:101BC00013C0319F02D6F08023C0319F62D6F0834
:101BD00033CFC2D0A168A11B1210A128A15022E25
:101BE000A168A11D2210A128A15022E0A168A11A1
:101BF000F3210A128A15022E0A168A1114220A12D9
:101C00008A15022ED72F313084006F088000008001B
:101C10002030B900BA00BB00BC00BD00BE00BF0050
:101C20006F08003C0319C2246F08013C0319762495
:101C30006F08023C03197D246F08033C03198A24B2
:101C40006F08043C031995246F08053C0319AA2466
:101C50006F08063C0319B324D72F080042276F08EA
:101C6000003C031908006F08013C0319CE266F08D9
:101C7000023C0319D3266F08033C0319D8266F08CA
:101C8000043C0319DD266F08053C0319E2266F08A2
:101C9000063C031908006F08073C03197526080065
```

```
:101CA0004227A022D72F08004227A0222030BD00C3
:101CB000D72F08004227B522D72F42274D2F0800E3
:101CC0004227CA22D72F08004227C623D72F4227F0
:101CD000E723D72F4227CA222030BD00D72F080084
:101CE0004227E122D72F4D2F080042278922D72FE4
:101CF0000123F822D72F4D2F08001C23F822D72FBD
:101D000004D2F08002C236D24D72F4D2F080033238F
:101D10006D24D72F4D2F08001F23F822D72F4D2FCA
:101D200008002223F822D72F4D2F08002C23D72F6D
:101D30004D2F08003323D72F4D2F08003A23D72FDC
:101D40004D2F08004227D72F4D2F08000823D72FEB
:101D50004D2F08000D23D72F4D2F08001223D72F0A
:101D60004D2F08001723D72F4D2F08002523F822C9
:101D70000D72F4D2F08004123F822D72F4D2F0800D1
:101D80006323D72F4D2F8423D72F4D2FA523D72F54
:101D90004D2F42274823D72F4D2F080042270824D4
:101DA000D72F4D2F080042272124D72F4D2F080071
:101DB00042273424D72F4D2F080042274924D72FFC
:101DC0004D2F080042276224D72F4D2F08004227AD
:101DD0006D24D72F4D2F08004227D72F4D2F0800F5
:101DE0004227CD24D72F4227EC24D72F422709257D
:101DF000D72F6D083F3C03191F2F6D083E3C031978
:101E0000242F6D083D3C03192E2F6D083C3C03190F
:101E100392F08006D083F3C03191F2F6D083E3C09
:101E20000319242F6D083D3C0319292F6D083C3CF4
:101E30000319332F6D08313C03193E2F08006F083A
:101E4000303EBF00D72F4D2F6F08303EBE00D72F3A
:101E50004D2F6F08303EBC00D72F4D2F6F08303EFE
:101E6000BD00D72F4D2F6F08303EBB00D72F4D2F11
:101E700008006F08303EBC00D72F08006F08303EC6
:101E8000B100D72F1030E50030308400203080000C2
:101E9000E50B4B2F0800840A472F1330F2008711FF
:101EA00007112A30E500E50B532F3830A300662FC9
:101EB0002830A300662F2830622F0C30622F0630A6
:101EC000622FCC2FA300662FA30E662F0712231AB2
:101ED00007168712A31A87160713231B07178713E2
:101EE000A31B87178715000087112A30E500E50B33
:101EF000772FF203123072020319582F1130720239
:101F000003195B2F103072020319642F0F30720215
:101F100003195D2F0E3072020319642F0D30720207
:101F200003195F2F0C3072020319642F0B307202F9
:101F30000319612F0A3072020319D92F0930720276
:101F40000319DC2F083072020319642F0730720264
:101F50000319DE2F063072020319E02F05307202DA
:101F60000319642F043072020319E52F0330720243
:101F70000319F32F023072020319642F0130720229
```

```
     :101F80000319F52F003072020319F82F2A30E500EB
     :101F9000E50BC82FF2037A2F2930E6002A30E5003E
     :101FA000E50BD02FE60BCE2FF20308007A2F0A3074
     :101FB000F20087110711C62F8030622F0715C62F38
  5  :101FC000303084000008A300622F37300402031968
     :101FD000F12F3F300402031908000230F207840A8F
     :101FE000E22F0711C62FC030622F0715840AC62FB3
     :061FF0000630F207E22FAB
     :10200000840185018601831606309F000E3085000D
 10  :1020100000308600831202308500B03086007B21BC
     :10202000FC3086007B21A03086007B21803086003A
     :102030007B21831628084E3C03192A2827083220C2
     :10204000A00027088120A100D020A70A2708280285
     :10205000031D1E282C088312F402033085002A3049
 15  :10206000EE00080082078034FF348034FF346C3483
     :102070008034FF348034FF346C3480346C3450341A
     :1020800055346034FF3460346C34AA349834873467
     :1020900080346534723487347234803487348034C9
     :1020A00098348734AA349834873480346534723451
 20  :1020B00087347234803487348034 9834AA3480343E
     :1020C000FF348034723465348034653 472 4AA3419
     :1020D0008034FF348034723465 480348734AA34D9
     :1020E0008034FF348034723465345F346534723444
     :1020F00080348734AA34983487348034FF34803471
     :10210000FF3482072434023424340234643448 4E3
     :1021100023448340234643424342434483 483497
     :1021200048340234483496341634163464343 3425
     :10213000323464343234323432343234323432343D
     :10214000643416341634643432343234643432 401
 30  :1021500032343234323432343234AA342434023415
     :10216000243424342434243424342434243424 4AF
     :1021700023424342434243424483424 434243 9D
     :10218000234243424342434243424342434243 B1
     :1021900024342434243424344834023448340 3 7B
 35  :1021A000FF30A6002008A200031DD8280030A6009A
     :1021B0002108A300A4012608A5002508831285068E
     :1021C000083160000000A20BF2282008A2002608B7
     :1021D000A5000130A4020318F4280130A302031C57
     :1021E0000800DD28A501E92800000000DD283F30B7
 40  :1021F000ED00221422210030AB00AA000330AC0015
     :10220000AD000130A20000302702031D1B290B3056
     :10221000EE000A128A151A2000000A168A1184217B
     :102220002208013C031907294108EF000A128A110C
     :1022300006125 A16222125142714D827D8272A30E9
 45  :10224000EE0008005408003C03192E2954080C3CE9
     :102250000319302954081 3C0319322980303429D6
```

```
:102260008130342982303429F0000A128A11A527DE
:102270000A16EF00C100C3006F08003C03194C2987
:102280006F08013C031954296F08023C03195D29AA
:102290006F08033C03196629123083l6A800A701B2
:1022A0000730AC0083126D2983162C30A800123041
:1022B000A7000A30AC0083126D2983164D30A800A8
:1022C0002C30A7000830AC0083126D2983164E30E5
:1022D000A800A7000230AC0083122208003C0319BA
:1022E0007329271C79290A128A15DA258A110A16F8
:1022F0007B2100000800FF30E400FF30E300E30B27
:102300007F29E40B7D2908008B130A128A15DA2530
:102310008A110A168B176F08C1003F30ED000800C4
:102320002030B0005330B1004530B2004C30B30023
:102330004530B4004330B5005430B6002030B7000B
:102340005330B8004F30B9005530BA004E30BB00A2
:102350004430BC002030BD002030BE002030BF0023
:1023600008002030B0004230B1005230B20041309D
:10237000B3004830B4004D30B5006030B60053308B
:10238000B7002030B8004C30B9005530BA004C309E
:10239000BB004C30BC004130BD004230BE00593063
:1023A000BF0008002030B0004830B1004F30B2000C
:1023B0004D30B3004530B4002030B5005330B60086
:1023C0005730B7004530B8004530B9005430BA0036
:1023D0002030BB004830BC004F30BD004D30BE0047
:1023E0004530BF0008002030B0005930B100413006
:1023F000B2004E30B3004B30B4004530B50045302C
:10240000B6002030B7004430B8004F30B9004F302C
:10241000BA004430BB004C30BC004530BD00203019
:10242000BE002030BF0008002030B0004E30B100A8
:102430004F30B2002030B3005330B4004F30B500FD
:102440005530B6004E30B7004430B8002030B900E7
:102450002030BA002030BB002030BC002030BD004E
:0A2460002030BE002030BF0008004D
:104200000B002D0001000100040005000B00000060
:10421000001000100000000000007001E000700003006D
:104220000000004000000400040000000600060076
:10423000006000600001000B0000000400000004005E
:1042400000400000006000700070006000300000004D
:1042500000400000004000400000000600080006003E
:104260000060005001400010000C0004000100020018
:104270000000000400010001003B00000001000500F7
:104280000090001000400020000000040000000200l8
:104290000010006000C0000000600010002000000002
:1042A00001001B00000001000200070000000200E6
:1042B00038000000020005000600000000400lE0097
:1042C0000000004000300000000000l0008000000DE
```

```
:1042D00001000000080000000200110000000200C0
:1042E00001000700000003001E000000030003009F
:1042F0000000000004002F0000000400040007007C
:06430000000001000200B4
:00000001FF
```

What is claimed is:

1. An apparatus for facilitating the remembrance of a user's dreams during a REM event in the user's sleep period comprising:

means for inputting data relating to the start time and end time of the user's sleep period;

electronic controller means remote from said user, said electronic controller means responsive to said means for inputting data to calculate the time of said REM event based on said start time and said end time of the user's sleep period;

means for waking the user associated with said electronic controller means; and means for recording a description of the user's dreams associated with said electronic controller means;

said means for waking the user and said means for recording activated by said electronic controller means to wake said user and record said description of the user's dreams at said calculated time.

2. An apparatus for waking a user during a REM event in the user's sleep period, comprising:

a microcontroller;

an alert device responsive to said microcontroller for waking said user;

a user input device associated with said microcontroller for inputting the start time and length of said user's sleep period to program said microcontroller to calculate the time of said REM event and activate said alert device at said calculated time.

3. The apparatus of claim 2 further comprising a recording device connected to said microcontroller, wherein said microcontroller is further programmed to activate said recording device during said REM event.

4. The apparatus of claim 3 wherein said recording device is voice activated.

5. The apparatus of claim 2 wherein the strength of said alert device is adjustable to wake said user during a REM event, but not during non-REM sleep.

6. The apparatus of claim 5 wherein said alert device is a flashing light.

7. The apparatus of claim 6 wherein the strength of said flashing light is adjustable with respect to one or more variables selected from the group consisting of flash intensity, flash frequency, flash duration and flash color.

8. The apparatus of claim 5 wherein said alert device is a speaker for playing an alert sound.

9. The apparatus of claim 8 wherein said alert sound is a melody.

10. The apparatus of claim 2 wherein said microcontroller is programmed to calculate the times of each REM event in a sleep period having 4 REM events and activate said alert device at said calculated times.

11. The apparatus of claim 2, wherein said microcontroller is programmed to calculate the times of each REM event in a sleep period having 5 REM events and activate said alert at said calculated times.

12. The apparatus of claim 2, wherein said microcontroller is programmed to calculate the times of each REM event in a sleep period having 6 REM events and activate said alert at said calculated times.

13. An apparatus for assisting the user in recording his or her dreams during a REM event in said user's sleep period, comprising:

a microcontroller;

a recording device responsive to said microcontroller;

an alert device responsive to said microcontroller to wake said user during a REM event, but not during non-REM sleep;

an input device associated with said microcontroller for inputting the start time and length of said user's sleep period; and said microcontroller programmable to calculate the time of said REM event during said sleep period, and activate said alert device and said recording device during said REM event.

14. The apparatus of claim 13 wherein said recording device is voice activated.

15. The apparatus of claim 13 wherein said alert device is a flashing light and the strength of said flashing light adjustable with respect to at least one variable selected from the group consisting of flash intensity, flash frequency, flash duration and flash color.

16. The apparatus of claim 13, wherein said alert device is a speaker for playing an alert sound.

17. The apparatus of claim 13, wherein said microcontroller is programmable to calculate the times of each REM event during said sleep period having 4 REM events, and activate said alert device and said recording device at said calculated times.

18. The apparatus of claim 13, wherein said microcontroller is programmable to calculate the times of each REM event during said sleep period having 5 REM events, and activate said alert device and said recording device at said calculated times.

19. The apparatus of claim 13, wherein said microcontroller is programmable to calculate the times of each REM event during said sleep period having 6 REM events, and activate said alert device and said recording device at said calculated times.

20. An apparatus for facilitating the investigation of the subject matter of the user's dreams during a REM event, comprising:

a microcontroller;

a predetermined pattern of REM events programmed in said microcontroller;

an input device connected to said microcontroller; and an alert enunciator connected to said microcontroller;

said microcontroller adapted to receive a sleep period from said input device, calculate the time of at least one REM event during said sleep period based on said predetermined pattern of REM events, and activate said alert enunciator at said calculated REM event time.

21. The apparatus of claim 20, wherein said enunciator comprises an aural alert to wake the user during REM sleep.

22. The apparatus of claim 20, wherein said enunciator comprises a visual alert to wake the user during REM sleep.

23. The apparatus of claim 22, wherein said visual alert comprises a plurality of differently colored LEDs.

24. The apparatus of claim 22, wherein said visual alert comprises a flashing light directed toward the user.

25. The apparatus of claim 24, wherein said flashing light is adjustable with respect to a variable selected from the group consisting of: flash frequency, flash length, flash intensity, flash color and combinations thereof.

26. The apparatus of claim 20, further comprising a recording system for the user to record statements upon being awakened by said alert enunciator.

27. The apparatus of claim 26, wherein said recording system comprises a microphone and a speaker associated with a record/playback chip, for recording an oral description of the user's dreams on said record/playback chip through said microphone and played back over said speaker.

28. The apparatus of claim 26, wherein said recording system is voice activated.

29. The apparatus of claim 20, further comprising a computer port and wherein said microcontroller is programmable, said computer port adapted to input and download programming instructions to and from said microcontroller.

30. An apparatus for facilitating the investigation of the subject matter of the user's dreams during a REM event, comprising:

a microcontroller;

an input device connected to said microcontroller; and an alert enunciator connected to said microcontroller, said alert enunciator having an intensity sufficient to wake the user during a REM event but not during non-REM sleep;

said microcontroller adapted to receive a sleep period from said input device, calculate the time of at least one REM event during said sleep period, and activate said alert enunciator at said calculated REM event time.

31. The apparatus of claim 30, wherein said enunciator comprises an aural alert to wake the user during REM sleep.

32. The apparatus of claim 30, wherein said enunciator comprises a visual alert to wake the user during REM sleep.

33. The apparatus of claim 32, wherein said visual alert comprises a plurality of differently colored LEDs.

34. The apparatus of claim 32, wherein said visual alert comprises a flashing light directed toward the user.

35. The apparatus of claim 34, wherein said flashing light is adjustable with respect to a variable selected from the group consisting of: flash frequency, flash length, flash intensity, flash color and combinations thereof.

36. The apparatus of claim 30, further comprising a recording system for the user to record statements upon being awakened by said alert enunciator.

37. The apparatus of claim 36, wherein said recording system comprises a microphone and a speaker associated with a record/playback chip, for recording an oral description of the user's dreams on said record/playback chip through said microphone and played back over said speaker.

38. The apparatus of claim 36, wherein said recording system is voice activated.

39. The apparatus of claim 30, wherein said intensity of said alert enunciator is sufficient to wake the user at approximately the end of a REM event but not during the beginning of a REM event.

40. The apparatus of claim 30, further comprising a computer port and wherein said microcontroller is programmable, said computer port adapted to input and download programming instructions to and from said microcontroller.

* * * * *